(12) United States Patent
Thompson et al.

(10) Patent No.: US 7,084,661 B2
(45) Date of Patent: Aug. 1, 2006

(54) SCANNING KELVIN MICROPROBE SYSTEM AND PROCESS FOR ANALYZING A SURFACE

(75) Inventors: Michael Thompson, Toronto (CA); Larisa-Emilia Cheran, Toronto (CA)

(73) Assignee: Sensorchem International Corporation, Toronto (CA)

( * ) Notice: Subject to any disclaimer, the term of this patent is extended or adjusted under 35 U.S.C. 154(b) by 0 days.

(21) Appl. No.: 10/296,507

(22) PCT Filed: May 18, 2001

(86) PCT No.: PCT/CA01/00717

§ 371 (c)(1),
(2), (4) Date: Feb. 28, 2003

(87) PCT Pub. No.: WO01/90730

PCT Pub. Date: Nov. 29, 2001

(65) Prior Publication Data

US 2003/0175945 A1    Sep. 18, 2003

(30) Foreign Application Priority Data

May 24, 2000   (CA) .................................. 2309412

(51) Int. Cl.
*G01R 31/26*    (2006.01)

(52) U.S. Cl. .................................................. 324/766

(58) Field of Classification Search ........ 324/750–751, 324/754, 762; 250/306–307; 73/105; 702/19–20
See application file for complete search history.

(56) References Cited

U.S. PATENT DOCUMENTS

| | | | | |
|---|---|---|---|---|
| 4,433,288 A | * | 2/1984 | Moore ........................ | 324/767 |
| 4,649,336 A | | 3/1987 | Bindner et al. | |
| 5,267,471 A | * | 12/1993 | Abraham et al. ............. | 73/105 |
| 5,336,887 A | * | 8/1994 | Yagi et al. ................... | 250/306 |
| 5,369,370 A | * | 11/1994 | Stratmann et al. .......... | 324/663 |
| 5,442,297 A | * | 8/1995 | Verkuil ....................... | 324/752 |
| 6,005,246 A | * | 12/1999 | Kitamura et al. ........... | 250/306 |
| 6,006,594 A | * | 12/1999 | Karrai et al. ................ | 73/105 |
| 6,073,485 A | * | 6/2000 | Kitamura .................... | 73/105 |
| 6,094,971 A | | 8/2000 | Edwards et al. | |
| 6,097,197 A | * | 8/2000 | Matsuyama et al. ........ | 324/754 |

OTHER PUBLICATIONS

W. Nabhan, B. Eqer et al., A. Broniatowski and G. De Rosny, "A high-resolution scanning Kelvin probe... measurements on the 100 n. scale", *Rev. Sci. Instrum.*, 1997, 68 (8), 3108.

(Continued)

*Primary Examiner*—Jermele Hollington
(74) *Attorney, Agent, or Firm*—Kathleen E. Marsman; Bored Ladner Gervais LLP

(57) ABSTRACT

A scanning Kelvin microprobe (SKM) system capable of measuring and analyzing surface characteristics of samples is provided. Also provided is a process of measuring and analyzing surface characteristics of samples. Further, there are provided uses of the SKM system in measuring and analyzing surface characteristics of conductors, semiconductors, insulators, chemicals, biochemicals, photochemicals, chemical sensors, biosensors, biochemical microarrays, microelectronic devices, electronic imaged devices, micromachined devices, nano-devices, corroded materials, stressed materials, coatings, adsorbed materials, contaminated materials, oxides, thin films, and self assembling monolayers.

4 Claims, 19 Drawing Sheets

OTHER PUBLICATIONS

M. Schmidt, M. Nohlen, G.,Bermes, M. Bomer and K. Wandelt, "A versatile Kelvin probe for dynamic work function change measurements during gas adsorption and *in situ* film growth experiments", *Rev. Sci. Instrum.*, 68, Oct. 1997, 3866.

M. Bömisch et al. "Atomic Force Microscope Based Kelvin Probe Measurements: Application To An Electrochemical Reaction", *J. Phys. Chem B*, 1997, 101, 10162-10165.

W.A. Zisman, "A New Method of Measuring Contact Potential Differences in Metals", *Rev. Sci. Instrum.*, 1932,3, 367-370.

P. Craig and V. Radeka, *Rev. Sci. Instrum.*, "Stress Dependence of Contact Potential: The ac Kelvin Method", 1970, 41, 2, 258.

N.A. Surplice and R.J. D'Arcy, "A critique of the Kelvin method of measuring work functions", *J. Phys.E: Sci. Instrum.*, 3, (1970), 477.

B. Ritty, et al., "Conditions necessary to get meaningful measurements from the Kelvin method", *J. Phys. E: Sci. Instrum.*, 15, 1982, 310.

I.D. Baikie, E. Venderbosch, "Analysis of stray capacitance in the Kelvin method", Rev.Sci.Instrum. 62 (3), 1991, 725.

O.A. Semenikhin et al., "Atomic Force Microscopy and Kelvin Probe Force Microscopy Evidence of Local Structural Inhomogeneity and Nonuniform Dopant Distribution in Conducting Polybithiophene", *J. Phys. Chem.* 100, 48, 1996, 18603.

I. Samec. W. Johnson, et al. "Kelvin probe measurements for chemical analysis: interfacial structure of electrodes exposed to the gas phase containing water vapour", *Sensors and Actuators*, B, 13-14 (1993) 741-742.

S. Lundgren et al., "A high-temperature Kelvin probe for flow reactor studies", *Rev. Sci. Instrum.* 66, 7, (1995) 3976.

C. S. Kumar, et al., "Automated reed-type Kelvin probe for work function and surface photovoltage studies", Rev. Sci. Instrum. 67 (3) (1996), 805.

H.A. Engelhardt, et al. "An accurate and versatile vibrating capacitor for surface and adsorption studies", *J. Phys E: Sci. Instr.* 19, (1977), 1133.

I.D. Baikie, et al. "Characterization of Oxides and Thin Films", *Mat. Res. Soc. Symp. Proc.* 309, (1993), 35.

M. E. McGovern et al. "Thiol functionalization of surfaces for biosensor development", M. Thompson, *Can.J.Chem.* 77 (1999), 1678.

L.M. Furtado et al. "Interactions of HIV-1 TAR RNA with Tat-Derived Peptides Discriminated by On-Line Acoustic Wave Detector", *Anal. Chem.* 71, (1999), 1167.

M. E. McGovern et al. "Pentafluorinated Probes for the X-ray Photoelectron Spectroscopic Study of Immobilized Bifunctional Silanes", *Anal. Chem.* 2000, 72, pp. 128-134.

M. Nonnenmacher, et al. "Kelvin probe force microscopy", *Appl. Phys, Lett.*, 1991, 58, (25), 2921.

M. Nonnenmacher, et al. "Surface investigations with a Kelvin probe force microscope", *Ultramicroscopy*, 1992, 42-44, 268.

M. Yasutake, "Improvement of Kelvin Probe Force Microscope (KFM) System", *J. Appl. Phys.*, 1995, 34, 3403.

M. Yasutake, et al. "Surface potential measurements using the Kelvin probe force microscope", *Thin Solid Films*, 1996, 279.

Cavic, et al. "Label-free detection of DNA probe microarrays by scanning Kelvin microprobe", Internet: CS2000 Conference Program, Abstract 56, Session AN3, Online, May 13, 2000, XP-002182470.

L-E. Cheran, H-D. Liess, M. Thompson, "Scanning Kelvin Microprobe in the Tandem Analysis of Surface Topography and Chemistry", *The Analyst*, 1999, 124, 961.

Cheran, et al., "Surface immobilized biochemical macromolecules studied by scanning Kelvin microprobe", *The Royal Society of Chemistry*, 2000,116, 23-34.

\* cited by examiner

Topographic image of 1μm step of Al on a Si wafer

CPD image of 1 μm step of Al on a Si wafer

Si surface (topography)

Si surface (CPD)

Contact potential image of oligonucleotide ($F_1$) attached to Si surface

Contact potential image of DNA duplex formation ($F_2$ hybridized to $F_1$)

topography
laser micromachining
5 micron lines
1 micron lateral step
(slinst.opj)

CPD image of silicone implant surface (exterior side)

CPD image of silicone implant surface (interior side)

SCANNING KELVIN MICROPROBE SYSTEM AND PROCESS FOR ANALYZING A SURFACE

This application is a 371 of international application PCT/CA01/00717 filed on May 18, 2001.

FIELD OF THE INVENTION

This invention relates to processes for measurement and analysis of surfaces utilizing Kelvin methodology, and more specifically to the development and use of an improved scanning Kelvin microprobe (SKM) for surface measurement and analysis.

BACKGROUND OF THE INVENTION

The Kelvin method for the measurement of work function can be employed for the analysis of a wider range of materials, at different temperatures and pressures, than any other surface analysis technique. Work function is a very sensitive parameter which can reflect imperceptible structural variations, surface modification, contamination or surface-related processes. The method is now regaining popularity[1-4] as a powerful technique because of its inherent high surface sensitivity, high lateral resolution due to the availability of nanometric precision-positioning systems, and improved signal detection devices. Unlike many other methods, the measurement of work function does not depend on an estimate of the electron reflection coefficient on the surface. Moreover, the technique does not use high temperature, high electric fields, or beams of electrons or photons. Being a non-contact and non-destructive method, it does not pose the risk of desorbing or removing even weakly-bound species from the surface. Furthermore, the Kelvin method is a direct measurement method requiring only a simple experimental set-up with no sample preparation.

When an electron is removed from a point within a material, the total change of thermodynamic free energy of the whole system is the difference between the change of the electrochemical potential of that material and the change of the electrostatic potential of the electron. If the electron is removed from a surface to a point in a vacuum, far from the outside surface so the surface forces have no more influence on the electron, this change of free energy is called the work function of that surface. The corresponding change when the electron is removed to another material that is in intimate electrical contact and thermal equilibrium with the first material, is called the contact potential difference (CPD). For example, when two different conductors are first brought into electrical contact, free electrons flow out of the one with the higher electrochemical potential (i.e., Fermi level) into the other conductor. This net flow of electrons continues until equilibrium is reached when their electrochemical potentials have become equal. The metal of higher work function (having originally a lower electrochemical potential) acquires a negative charge, the other conductor being left with a positive charge. When the whole system reaches thermodynamic equilibrium, the resulting potential difference is the CPD and is equal to the difference between their work functions.

In order to measure the CPD it is necessary to connect the conductors. A direct measurement with a voltmeter included in the circuit is not possible, since the algebraic sum of all the CPDs in the circuit is zero. Thus, CPD must be measured in an open circuit i.e., using a dielectric such as a vacuum or air between the conductors.

The Kelvin method is based on a parallel plate capacitor model: a vibrating electrode suspended above and "parallel" to a stationary electrode. The sinusoidal vibration changes the capacity between plates, which in turn, gives a variation of charge generating a displacement current, the Kelvin current, proportional to the existing CPD between the electrodes.

The last century witnessed a continuous process of improving and modification of the Kelvin probe in order to adapt it for particular applications[5-10]. The probe has been used in surface chemistry investigations, surface photo voltage studies, corrosion, stress, adsorption and contamination studies and was adapted for measurements in liquids, at high temperatures, in ion or electron emitting samples or in an ultra high vacuum environment[11-15]. The problem of conducting measurements at the micrometer and sub-micrometer level has been overcome with the advent of SKM format which offers a new and unique tool to image the electrical potential on surfaces at the micrometer and sub-micrometer level. It has also been possible to develop an SKM instrument that is capable of generating both CPD and surface topographical images in tandem[1]. Such equipment not only provides an electrical image of a surface, but also generates a truly tandem topographical image. Accordingly, electrical information can be integrated fully with chemical and morphological details, an extremely valuable feature for the users of the surface characterization technologies.

However, to measure the CPD on a small scale with high precision it is necessary to control closely the distance between the tip and the sample. This has been initially achieved by processing the harmonics of the Kelvin current. However, this approach leads to instability and is unreliable.

SUMMARY OF THE INVENTION

It is an object of the present invention to obviate or mitigate at least one disadvantage of prior art processes, systems and methods applying SKM for microanalysis of surfaces.

The invention provides a scanning Kelvin microprobe system for analyzing a surface of a sample, the system comprising: a tip with a predetermined work function for exploring a surface of the sample, and for extracting Kelvin current from the local capacitor formed between the tip and the sample; a scan table for placing the sample thereon; a micropositioner for moving the scan table in x and y directions, a piezoelectric translation stage attached to the scan table for moving the sample in the z direction for maintaining a constant sample-tip distance; a charge amplifier for converting the Kelvin current extracted by the tip into a voltage; a first lock-in amplifier tuned at a first frequency for measuring the voltage and generating a contact potential difference image signal; a second lock-in amplifier tuned at a second frequency for monitoring sample-tip distance and for generating a topographic image signal, the second frequency being above the first frequency; and a controller for controlling the micropositioner.

The invention further provides a process for analyzing a surface of a sample using a scanning Kelvin microprobe system, comprising the steps of: placing a sample on a scan table; exploring a surface of the sample with a tip having a predetermined work function; extracting Kelvin current from a local capacitor formed between the tip and the sample; amplifying the Kelvin current extracted by the tip; measuring the Kelvin current and generating a contact potential difference signal using a first lock-in amplifier tuned at a first frequency; and monitoring distance between the sample and the tip and generating a topographic image signal using a second lock-in amplifier tuned at a second frequency, the second frequency being above the first frequency.

The SKM system of the invention uses a higher frequency (sample-tip capacitance detection) to control the sample-tip distance, thus, making the process stable and reliable. The automated monitoring of the contact potential and topography was achieved using 2 lock-in amplifiers tuned respectively on the vibrational frequency and on the capacitance-detection frequency. This means that the monitoring of the sample-tip distance is no longer achieved by processing the harmonics of the CPD signal as taught by the prior art, but by measuring the sample-tip capacitance at a frequency above the vibrational frequency. This approach solves the instability and unreliability problems that affect the prior art. The current prototype has a superior lateral resolution achieved by employing amplifiers capable of detecting low-level currents extracted by extremely fine tip probes having an apex radius of curvature below 100 nm. The invention advantageously comprises a data acquisition and imagining system. Further, the null-condition measurement according to the invention avoids the strong electric fields that affect the surface of the specimens in prior art apparatuses. This is also an advantage over the force microscopes operating in Kelvin mode that develop extremely high local electrical fields ($10^9$ V/m range), thus affecting both the local distribution of charges and the spatial conformation of the investigated molecules.

The scanning instrument developed is capable of CPD measurement to a lateral resolution of 1 micron and can display a resolution of 1 mV. The instrumentation according to the invention fulfils a long-standing need for high resolution measurements. With this instrument, it is now possible to generate new knowledge and applications in surface physical chemistry and material characterization. Advantageously, the technique is non-destructive. It can be used to examine a wide range of substrates whether they are conductors, semiconductors or insulators. The invention has applications in many technical fields such as surface chemical analysis, photochemical studies, corrosion, stress, triboelectricity, polymers and ferroelectric materials, adsorption and contamination, nano-devices, microelectronic fabrication, biochemical microarrays and biosensor technology.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
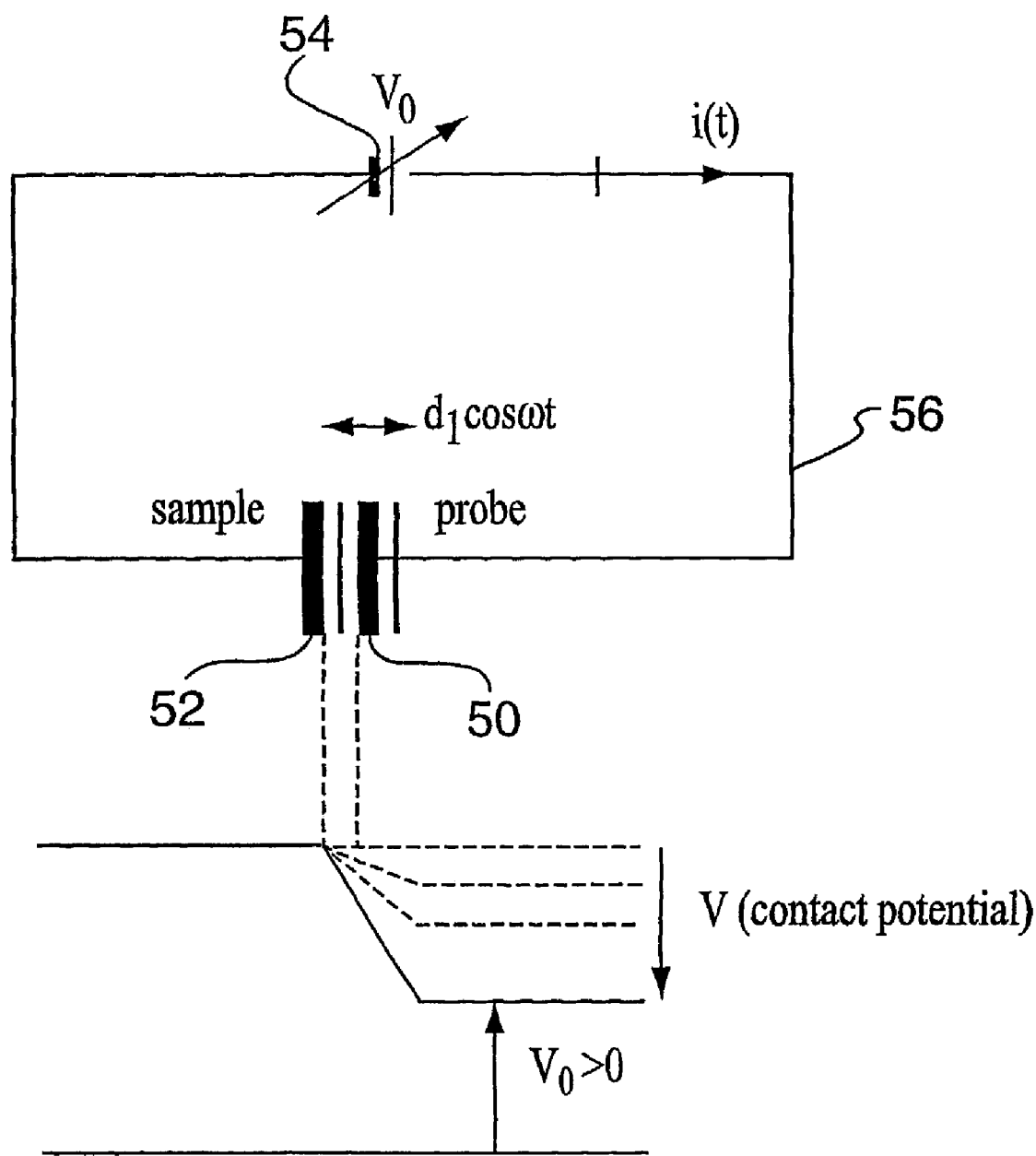
FIG. 1 is a diagrammatic illustration of the measurement of contact potential difference CPD according to the invention.

The invention relates to a scanning Kelvin microprobe system for analyzing a surface of a sample. The system comprises a tip with a predetermined work function for exploring the surface of the sample. The tip extracts Kelvin current from the local capacitor which is formed between the tip and the sample. The sample is placed on a scan table, and a micropositioner is used to move the scan table in x and y directions, allowing the tip to explore the surface. A piezoelectric translation stage is attached to the scan table, and is used to move the sample upwardly or downwardly toward or away from the tip, so as to maintain a constant sample-tip distance. The system further comprises a charge amplifier for converting the Kelvin current extracted by the tip into a voltage. A first lock-in amplifier is provided, which is tuned at a first frequency. The first lock-in amplifier measures the voltage and generates a contact potential difference image signal. A second lock-in amplifier is also provided, which is tuned at a second frequency. The second lock-in amplifier monitors sample-tip distance and generates a topographic image signal. The system also comprises a controller for controlling the micropositioner.

The invention also relates to a process for analyzing the surface of a sample using a scanning Kelvin microprobe system. The process involves placing a sample on a scan table, and exploring the surface of the sample with a tip having a predetermined work function. Kelvin current is extracted from a local capacitor formed between the tip and the sample, and the Kelvin current extracted by the tip is amplified. The amplified Kelvin current is measured and from this measurement, a contact potential difference signal is generated using a first lock-in amplifier tuned at a first frequency. The distance between the sample and the tip is monitored, a topographic image signal is generated using a second lock-in amplifier tuned at a second frequency. The second frequency is above the first frequency. The steps of the process may be controlled using a software program capable of opening a file, initializing a card and a motor, starting first and second lock-in amplifiers, bringing the tip down, scanning the sample, bringing the tip up, writing data in a file, and closing the file.

The sample to be analyzed according to the invention can a conductor, semiconductor, insulator, chemical, biochemical, photochemical, a chemical sensor, a biosensor, a biochemical microarray, a microelectronic device, and electronic image device, a micromachine device, a nano-device, a corroded material, a stressed material, a coating, an adsorbed material, a contaminated material, an oxides, a thin film or a self assembling monolayer.

The scan table is movable by any requisite amount so as to allow exploration of a sample surface, for example by about 200 nm in either the x or y direction. The scan table may optionally have course and fine adjustment, for example, coarse adjustment of about 100 nm and fine adjustment of about 4 nm.

A data acquisition system may be incorporated into the scanning Kelvin microprobe system, for acquiring the contact potential difference image signal and said topographical image signal.

The controller comprises software capable of opening a file, initializing a card and a motor, starting the first and the second lock-in amplifiers, bringing the tip down, scanning the sample, bringing the tip up, writing data in a file, and closing the file.

Kelvin current is generated when two electrodes or plates are brought in electrical contact with a measuring device and the Fermi levels of two electrodes equalize. The Kelvin current is a measure of contact potential difference (CPD) of the two electrodes.

Contact potential difference is the difference between the work functions of two materials in contact. Measurement of the CPD thus affords a method of measuring work function differences between materials. In order to measure the CPD it is necessary to connect the materials. A direct measurement, for instance with a voltmeter, requires a circuit shortened by a measurement device. However, in a closed circuit CPD cannot be measured directly, as the sum of the three interfacial differences would be zero, except for the case where the interfaces have different temperatures. Thus, CPD is measured in an open circuit, for example using a dielectric medium such as a vacuum or air.

Work function is the work required to extract an electron from the Fermi level to infinity.

A local capacitor is formed between the tip and the sample. The tip extracts Kelvin current from this local capacitor. A capacitor is capable of storing charges, formed by arrangement of two conductors or semiconductors (electrodes or plates) separated by a dielectric medium, such as air or a vacuum.

Capacitance is the property of a material whereby it stores electric charge. If an isolated conductor is placed near a second conductor or a semiconductor but is separated from it by air or some other insulator, the system forms a capacitor. An electric field is produced across the system and this field determines the potential difference between the two plates of the capacitor. The value of the capacitance of a given device is directly proportional to the size and shape (area) of the electrodes and the relative permittivity of the dielectric medium, and inversely proportional to the distance between the two plates. According to the invention, the tip and the sample act as the two plates of the capacitor, and air is the dielectric medium The tip of the scanning Kelvin microprobe system according to the invention is used to scan a sample and to extract Kelvin current from the capacitor formed between the tip and the sample. The tip can be made of any suitable material with a known work function, for example, tungsten. In one embodiment of the present invention, the tip is a guarded microelectrode having the apex radius of curvature less than about 100 nm, and optionally in the range of about 50 nm.

The sample is placed on a scan table, which is capable of moving in the x, y, and z directions. The micropositioner provides a means for moving the scan table in x and y directions, and expediently comprises a computer-related device. A translation stage is used to move the scan table in z direction, that is upwardly (closer to) or downwardly (further from) the tip. By the terms upwardly and downwardly, vertical distance is not implied, although the z direction may optionally be the vertical direction. In one embodiment of the invention, the translation stage is a piezoelectric translation stage. Particularly, the translation stage can be controlled by piezoelectricity.

The charge amplifier, which may include a series of amplifiers, such as a pre-amplifier plus a charge amplifier, allows magnification of an input electrical signal for output. In one embodiment of the present invention, the charge amplifier is an ultra low noise charge amplifier.

The lock-in amplifiers are detectors that respond only to an input signal having a frequency synchronous with the frequency of a control signal. A lock-in amplifier can be used to detect a null point in a circuit. According to the present invention, a first lock-in amplifier and a second lock-in amplifier are used. Each is tuned to a separate frequency, and the frequencies are non-interfering. The first frequency can be any from about 1 to about 20 kHz, while the second frequency can be any from about 100 to about 500 kHz. The second frequency is above the first frequency, so that the two frequencies are non-interfering.

The controller is an electronic device used to control the operation of the system. Optionally, the controller comprises a software program, and the controller may be incorporated within a hardware component.

The system according to the invention can be used for characterization and analysis of surfaces of materials, based on the variation of work function values associated with interfacial properties. This variation of work function is determined by the measurement of contact potential using the Kelvin probe method. This technique is founded on a parallel plate capacitor model, where one plate possesses a known work function and is used as a reference, while the material with unknown work function represents the other plate. An embodiment of the present invention is an SKM instrument that is capable of CPD measurement to a lateral resolution of 1 micron and displays a resolution of 1 mV. A unique feature of the instrument is its capability to generate both CPD and surface topographical maps in a tandem fashion reliably. Further, the method is non-destructive.

The scanning Kelvin microprobe (SKM) according to the invention can be used as a unique tool for investigating the physics and chemistry of surfaces. The instrument has application in a number of fields, including but not limited to, chemical sensors and biosensors, biocompatibility, microelectronic fabrication and characterization, electron imaging, micromachining, corrosion and coatings, adsorption and contamination, and characterization of oxides, thin films, and self-assembling monolayers.

One application of the SKM is in the investigation of interfacial phenomena in biosensor technology, especially the electrostatics of DNA on surfaces. The SKM can scan surfaces of biomaterials, including biosensors, for the spatial location of moieties such as proteins and oligonucleotides. These biological species carry a significant charge which can lead to highly significant differences in surface potential related to specific molecular reactions.

Another application of the SKM technology is in characterization of many kinds of materials such as conductors, semiconductors or insulators. The work function of a semiconductor surface involves the work function under flat band conditions and the surface barrier height associated with the filling of surface carrier traps. The work function of semiconductors depends on the crystallographic orientation, the atomic structure of the surface, and the history of surface processing and treatment. Thus, SKM can be used for several applications in semiconductor technology including the determination of surface potential fluctuation associated with charged grain boundaries, the distinction between regions of different chemical nature or composition, and two-dimensional dopant profiling.

The SKM technology according to the invention can be used to solve material engineering problems such as metal-semiconductor contacts or investigate the integrity of electrodes microelectronically deposited on semiconductors and polymers such as teflon (poly(vinylidene difluoride), PUDF, devices). Electronic image printing is a technology that involves electronic "writing" of latent images in drums with mixed polymer/carbon black surfaces. The instrument can provide both unique information on topography and electrostatic potential of electronic writings.

The SKM technology according to the invention is also a powerful tool for the study of surface morphology, structural variations, surface modification, electrochemical surface reactions and the local determination of various surface parameters. With respect to the characterization of oxides and thin films e.g., in terms of preparation methods, surface roughness, adsorption processes, thin film monitoring, residual surface contamination, the technique has several applications in areas such as control of thin film quality, detection of surface morphology, interface quality, metal contamination, and in studying fundamental processes such as sputtering, annealing, and diffusion.

The SKM according to the invention can be used in chemical analysis, especially in studies of the interfacial structure of electrodes such as electronic work function of the metal, changes in surface potential of the metal caused by the solvent ions, solvent contribution to the electrical potential difference at the metal/solution interface, and the surface dipole potential of the solution.

The technique can also be used to measure corrosion potential without touching the particular surface under examination. Up to the present time, because of limited lateral resolution, only large-area samples have been investigated. Using the SKM technique according to the invention such studies can be performed at the micron and sub-micron scale, which can lead to a better understanding of corrosion phenomena.

The SKM technology disclosed herein can also be used in contact potential measurements of self-assembling monolayer films. These monomolecular films create a surface potential, which depends on the packing density of the molecules, therefore, the SKM can assess the dipole density of Langmuir-Blodgett films or other self-assembling films. The technology can also be employed for the study of dipole layers and charge separation at interfaces under special conditions such as illumination or temperature changes. The measurement of the stress dependence of contact potential is also possible. When a metal is compressed, the resulting change in the volume of the lattice serves to limit the volume available to the conduction electrons. These changes in electronic energy (i.e., shifts of Fermi level) are manifested in shifts in the work function of the metal. These shifts can be detected by contact potential measurements using the SKM.

Development of an Improved Scanning Kelvin Microprobe System

The Kelvin method is based on the measurement of work function by a configuration consisting of a vibrating electrode suspended above and parallel to a stationary electrode. The sinusoidal vibration of one plate alters the capacity between the plates resulting in a Kelvin current, which is proportional to the existing CPD between the plates.

FIG. 1 shows the principle of the Kelvin method used in the present invention. The instrument shown has a vibrating tip (50) made of material with a known work function such as tungsten, which explores, point by point, the surface of the sample (52), extracting the Kelvin current from the local capacitor formed under the tip. When a thermodynamic equilibrium is established, a CPD appears between the two "plates" as a voltage V, or contact potential and the capacitor is charged. Since V remains constant, but the distance between the tip and the sample changes, the charge on the plates changes too. The tip (50) has a sinusoidal vibration, so the separation distance between the plates is:

$$d(t) = d_0 + d_1 \cos \omega t \tag{1}$$

where $d_0$ is the rest position and $d_1$ is the amplitude of the vibration. The frequency of the vibration is set at $f_1 = 2$ kHz. The capacity is then:

$$C(t) = \frac{\varepsilon A}{d(t)} = \frac{\varepsilon A}{d_0 + d_1 \cos \omega t} \tag{2}$$

wherein A is area of a plate, $\varepsilon$ is the dielectric constant, and t is the time. An adjustable DC voltage source, $V_0$ (54) is inserted in the circuit (56). The capacitor charging process causes a current in the measurement device, the Kelvin current:

$$i(t) = \frac{d\,Q(t)}{dt} = (V + V_0) \frac{\varepsilon \omega d_1 A \sin \omega t}{(d_0 + d_1 \cos \omega t)^2} \tag{3}$$

If the contact potential is compensated by the variable voltage source (54), there will be no current flowing in the circuit (56). This compensation is detected as a null-condition by a sensitive lock-in amplifier.

Figure 2:
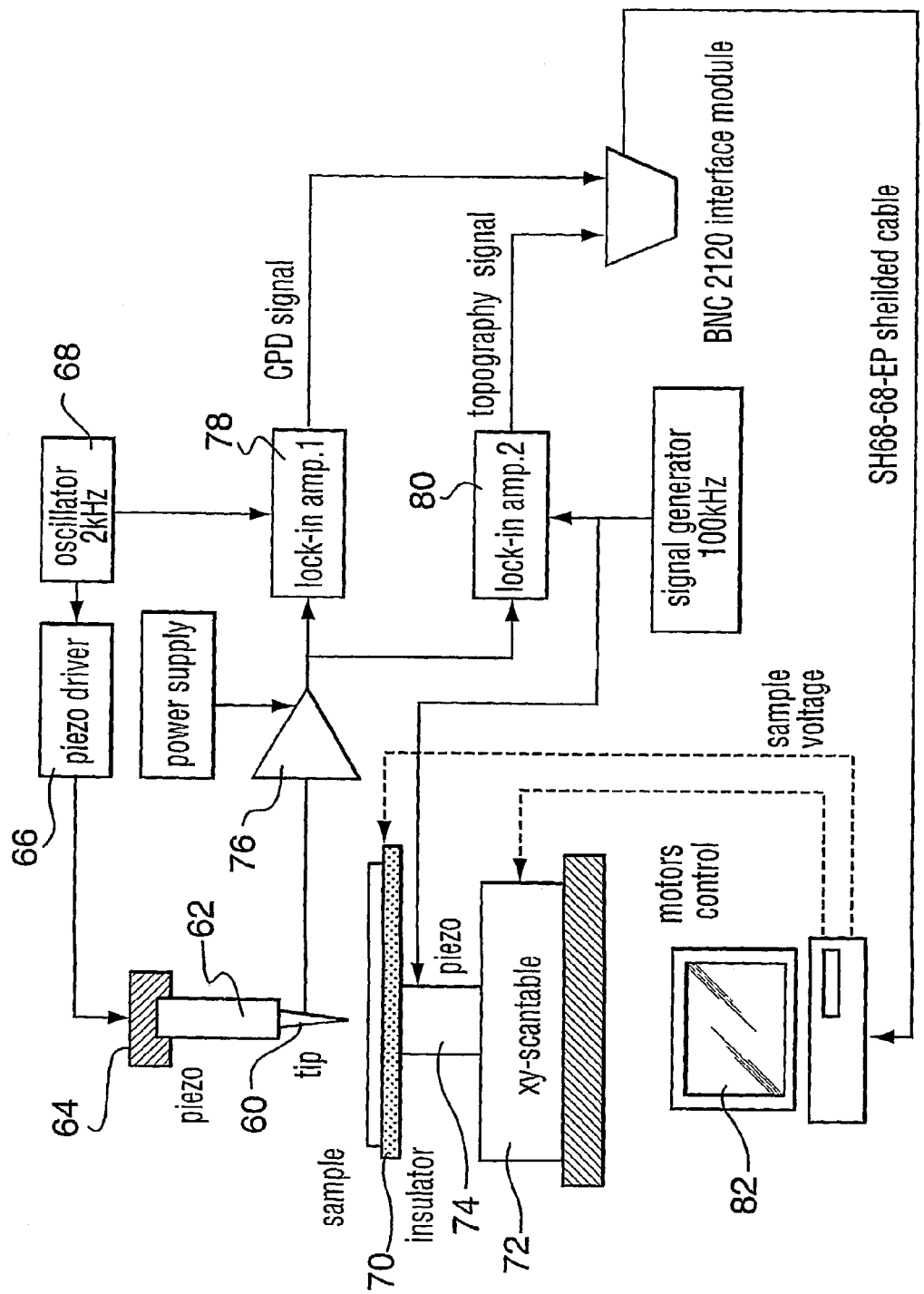
FIG. 2 is a schematic drawing of the instrument used in exemplary embodiments of the invention described herein.

FIG. 2 presents a schematic diagram of the instrument of an embodiment of the present invention. The system comprises of the following components: a scanning system having a tip (60), tip holder (62), piezoelectric element (64), piezoelectric element driver (66); vibrational frequency generator or oscillator (68), insulator (70), and a scan table (72) controlled by a micropositioner; a sample-tip distance control unit having a piezoelectric translation stage (74) and a capacitance-detection frequency generator; a measurement system having an ultra low-noise charge amplifier (76), a first lock-in amplifier (78) for measuring the voltage and generating a contact potential difference image signal, a second lock-in amplifier (80) for monitoring sample-tip distance and for generating a topographic image signal, vibrational frequency generator, and capacitance-detection frequency generator; a signal collection unit (82) having an interface module for interfacing the measuring system with a data acquisition (DAQ) board installed inside the computer; and a computing device for controlling the system.

A sample is placed on the scan table. The scan table is movable in the directions of the x-axis and the y-axis in order to have the sample scanned. The position of the scan table is adjusted by a micropositioning system (Nanonics, Israel)) which moves the scan table in x and y directions with a coarse resolution of 100 nm (closed loop DC motor) and a fine resolution of 4 nm (closed loop PZT drive), respectively. The control of the micropositioning system is achieved by a motor controller board installed in the computer. A piezoelectrically driven translation stage is mounted on the top of the scan table. The stage moves along the z-axis in order to maintain a constant distance between the tip and the sample.

The tip is attached to the piezoelectric element via the tip holder. The frequency of the vibration, $f_1$, to vibrate the tip, is generated by a frequency generator (oscillator) and is then fed into the vibrating piezoelectric element (Topometrix, California, U-SA) through the piezoelectric driving amplifier (I. P. Piezomechanik, Germany).

The Kelvin current extracted by the tip is converted to a voltage and amplified by means of an ultra low-noise preamplifier and a charge amplifier (A250+A275,Amptek Inc. USA). This voltage is fed at the entrance of the two lock-in amplifiers.

The first lock-in amplifier (SR530,Stanford Research Systems, USA) is tuned at $f_1$ and used to obtain the CPD signal. The $f_1$ may range from 1–20 kHz. The output voltage of the CPD lock-in amplifier is returned to the probe in a feedback loop (not shown). For large enough values of the open loop gain, the contact potential value is given directly by the output voltage of the lock-in amplifier.

The distance between the sample and the tip is monitored via capacitative control at a frequency above the vibration frequency $f_1$. The $f_2$ may range from 100–500 kHz. A small AC voltage (100 mV at frequency, $f_2$=100 kHz) is added in the circuit and the resulting Kelvin current between the tip and the sample is detected by a second lock-in-amplifier (SR530, Stanford Research Systems, USA) tuned to $f_2$. The tip-sample capacitance is kept constant by returning the output signal of the second lock-in amplifier to the piezoelectric translation stage. This signal is also used to obtain the topographical image of the sample.

The data acquisition and signal processing is done with the data acquisition board (PCI-6110) installed in the computer. All electric cables are carefully shielded and a BNC 2120 interface module is used for connections. The BNC 2120 interface module is a connector module interfacing the measuring system with the DAQ (data acquisition) board installed inside the computer. It contains a function generator, BNC connectors for analog input channels, analog output, digital input/output The system is controlled by a computing device having a PCI-6110 DAQ board (National Instruments), the motor controller C-842.20DC and the LabView programs (version 6I).

The exterior compensating voltage reduces the Kelvin current to zero. To measure the CPD on a small scale with high precision it is necessary to control closely the distance between the tip and the sample. This has previously been achieved by separation of the harmonics of the Kelvin current. However, this prior art approach leads to instability and is unreliable. The SKM system disclosed herein used instead a higher frequency (sample-tip capacitance detection) to control the sample-tip distance, thus, making the process stable and reliable.

The equipment construction, testing and adjustment of the prototype are conducted to ensure performance of the instrument and to assess its use in different applications. In order to calibrate the instrument and to verify the correct function, a number of metallic surfaces including Pt, Au, Ag, Sn, Pb and Al were examined. Patterned surfaces were obtained by sputtering of Pt layers on Ag and Si, Au layers on Pd and Ag, and metals on silicon and mica substrates. Conductive highly ordered-pyrolitic graphite and clean semiconductor surfaces (silicon) were also investigated. Contact potential images of dielectric materials such as mica, Teflon, silanized surfaces, NaCl and CsCl-treated substrates proved that the instrument can measure insulating surfaces. A theoretical explanation can be provided for this particular kind of measurement, based on combined dielectric layers of air and dielectric material between the metallic tip and the metallic table of the SKM. Biomolecules such as DNA, collagen, and other proteins deposited on different types of substrate were also studied.

A number of technical problems were solved in arriving at the SKM methodology disclosed herein.

It was necessary to clarify the true basis of the measurement of work function since major discrepancies exist in the literature with respect to "calibration" of contact potential differences as the measured contact potential can be significantly altered by the adsorption and contamination of surface layers. Quantitative interpretation of such data is difficult or even meaningless as evidenced by the large discrepancies found in compilations of work function values. Experimental measurements of CPD found in the literature show wide variations (the value for gold, for example, ranges from 4.68 to 6.24 eV). That is why, in order to find absolute values of work function of different materials, a special high-vacuum chamber can be attached to the system and carefully cleaned surfaces are beneficial are used. However, many applications do not require absolute values of CPD. They require only a simple indication of the electric charge distribution or a modified configuration of the local charges due to a subsequent physical or chemical treatment on the particular surface under investigation. These determinations can be performed in air and do not require special experimental conditions. This is the case with the SKM disclosed herein as an embodiment of the present invention, which is considered to constitute a major advantage when it comes to facile measurement performed without elaborate sample preparation.

Being a non-modulated SKM, the previous instrument was unable to fully compensate the measured CPD, since it depended on a voltage between the sample and tip to generate a Kelvin current needed for the distance control circuit. The sample voltage, a constant in the −5V to +5V range, could not balance the real value of the CPD. A null-condition (i.e., a perfect match between the real value of the CPD and the existing sample voltage) would, thus, cause a breakdown of the distance control system. Accordingly, the prior art instrumentation did not allow measurement of CPD directly. The CPD value generated by the instrument was near to, but was not the actual CPD. It was related to the CPD by a linear function. By conducting a two-point calibration, using two materials with a known and stable work function the inventors could determine the slope and offset of this line. By applying the linear function, the output of the SKM could be converted to the real value of the CPD. However, two-point calculation required for every measurement was time-consuming. Further, the inventors were confronted by the fact that an imperceptible change in any of the relevant parameters such as the vibration amplitude sample voltage, tip size or mean tip-sample distance could altered the parameters of the linear function. Thus, the calibration itself became a potential source of errors. With the prior art instrumentation[1], for any change in probe size, the Kelvin current would become so small that it would be impossible to detect, due to an extremely unfavorable signal/noise ratio. Further, due to outdated electronic solutions on the analog and digital circuitry the system soon became extremely unstable requiring considerable time to reliably generate clear and complete images.

For the reasons specified above and to benefit from recent advances in electronic technology, the inventors decided to build a modulated SKM that would obviate one or more problems described above and enable measurements under null-conditions. In order to achieve this, all electronic controls had to be modified by using high performance devices (such as charge amplifiers and lock-in amplifiers). This led to the inventive instrumentation disclosed herein.

The scanning Kelvin microprobe prototype was also modified to improve spatial resolution. The initial 20–50 µm resolution has been significantly enhanced to 1 µm by using sharper tungsten tips as probes. Additionally, to shield the electrode against parasitic electrical fields, guarded microelectrodes were developed. The shield is interrupts the circular lines of the electric field developing in the entire space between the metallic tip and metallic table by confining the field only in the apex aperture area. This also improves the sensitivity and lateral resolution of the probe. Electron microscopy is used to characterize the quality of the vapor deposition procedure used in order to form the guarded tip.

Figure 3:
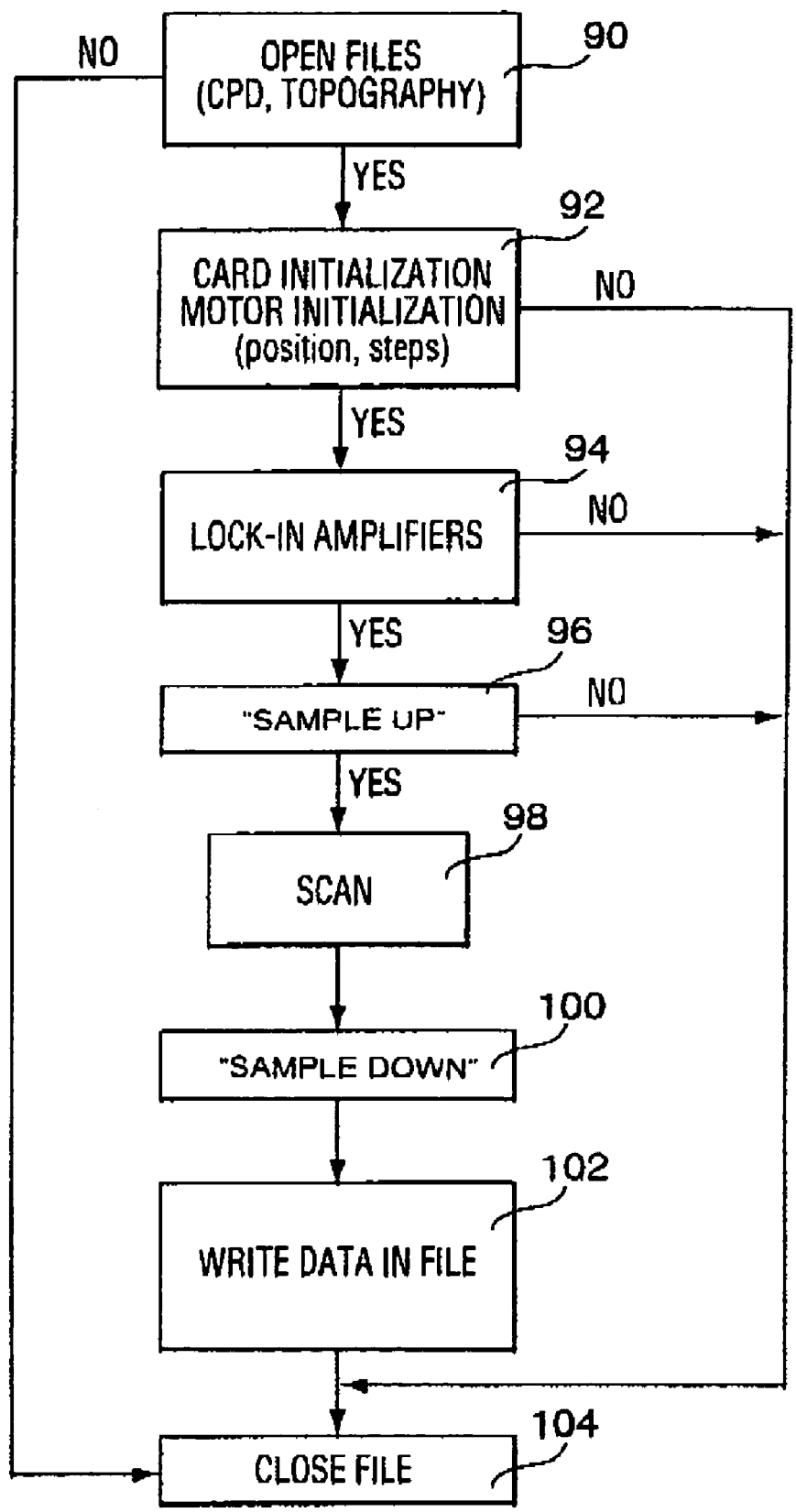
FIG. 3 shows a flow chart of a software program developed to control an SKM system according to an embodiment of the invention.

FIG. 3 shows a flow chart of a software program developed to operate the system according to the invention. The software was developed in LabView language (version 6i, National Instruments, USA) so the actual front panel of the SKM is displayed on the computer screen, the controls are available using the computer mouse, and the measuring develops in real time in graphic fashion on the screen, The virtual front panel is supported by the general block diagram behind it. The program controls the communication protocols between the hardware components, the motion of the micropositioning system, the vibration and translation of the tip and the piezoelectric table, the functioning of the feedback loops and the whole data acquisition protocols, and saves the measured data in the files. The measured data are processed and analyzed using the image processing software (version 6.1, OriginLab, USA) to obtain 2D or 3D pictures of both CPD and topography images.

As illustrated in FIG. 3, files are opened (90) to receive data relating to either the CPD image or the topography of the sample surface. A card and motor initialization step (92) allows for control of the SKM system. Data from the first and second lock-in amplifiers are obtained (94) and tip movement (96) in the z direction to approach the sample is effected on this basis. The sample is scanned (98), and the tip can be moved in the z direction (100) to retract from the sample. The data obtained is written to the files opened (102), and the process may be either repeated or terminated, in which case the file is closed (104).

EXAMPLES

The invention is further described, for illustrative purposes, in the following specific Examples.

Example 1

Characterizing Metals

A number of metallic surfaces including Pt, Au, Ag, Sn, Pb and Al are examined. Patterned surfaces are obtained by sputtering of Pt layers on Ag and Si, Au layers on Pd and Ag, and metals on silicon and mica substrates.

Figure 4:
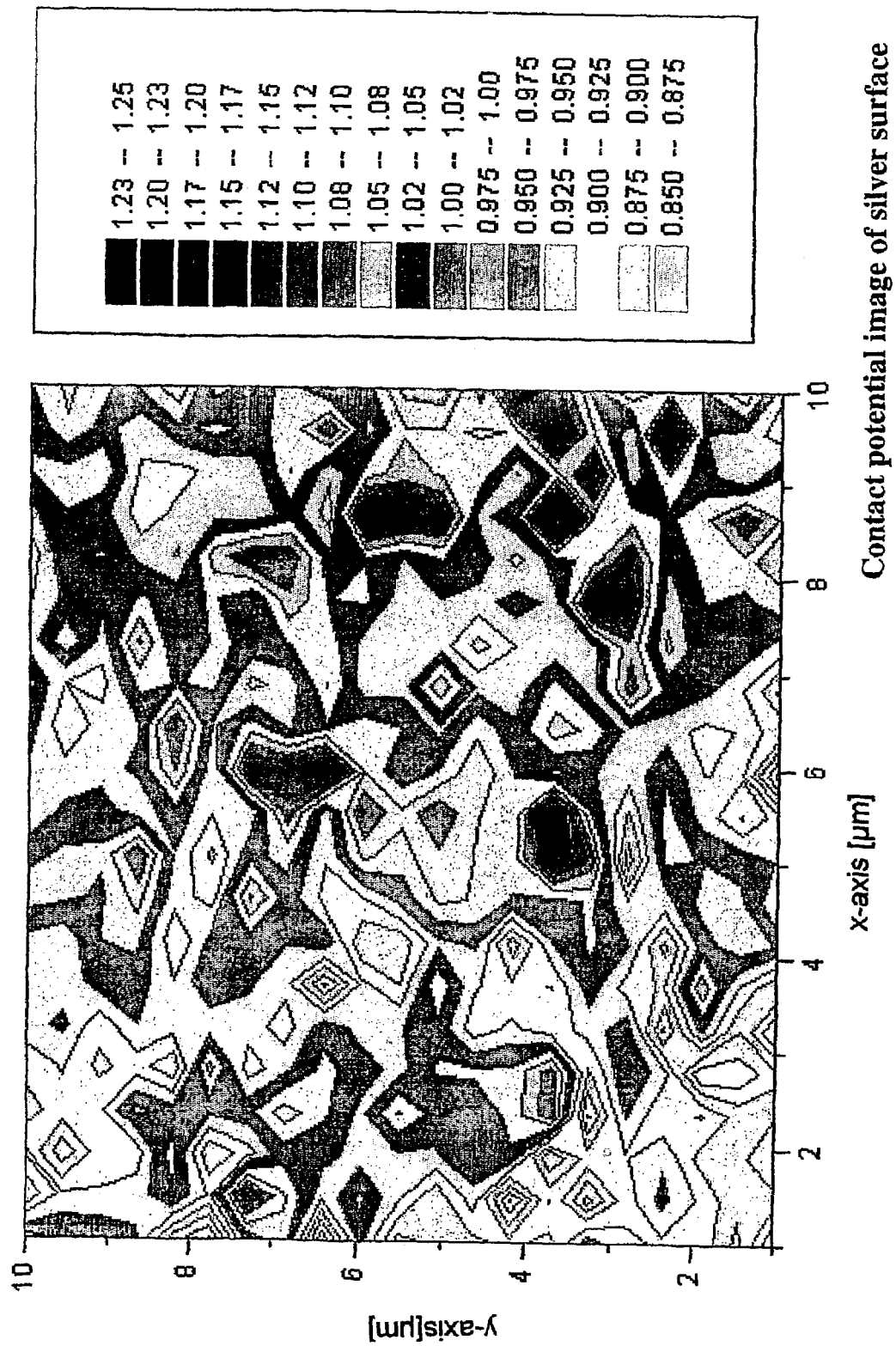
FIG. 4 is a CPD image of a silver surface.
Figure 5:
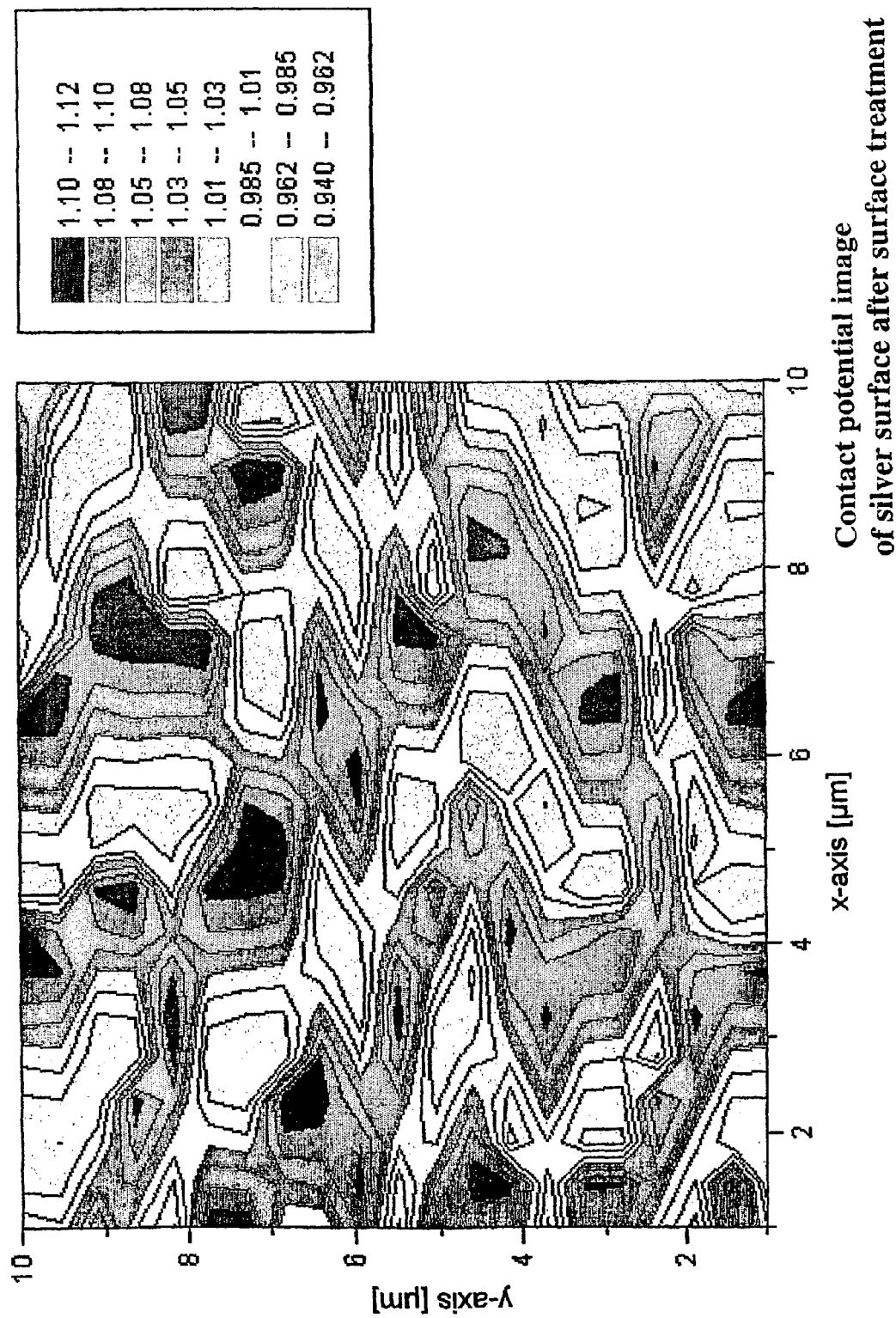
FIG. 5 is a CPD image of a silver surface after surface treatment.
Figure 6:
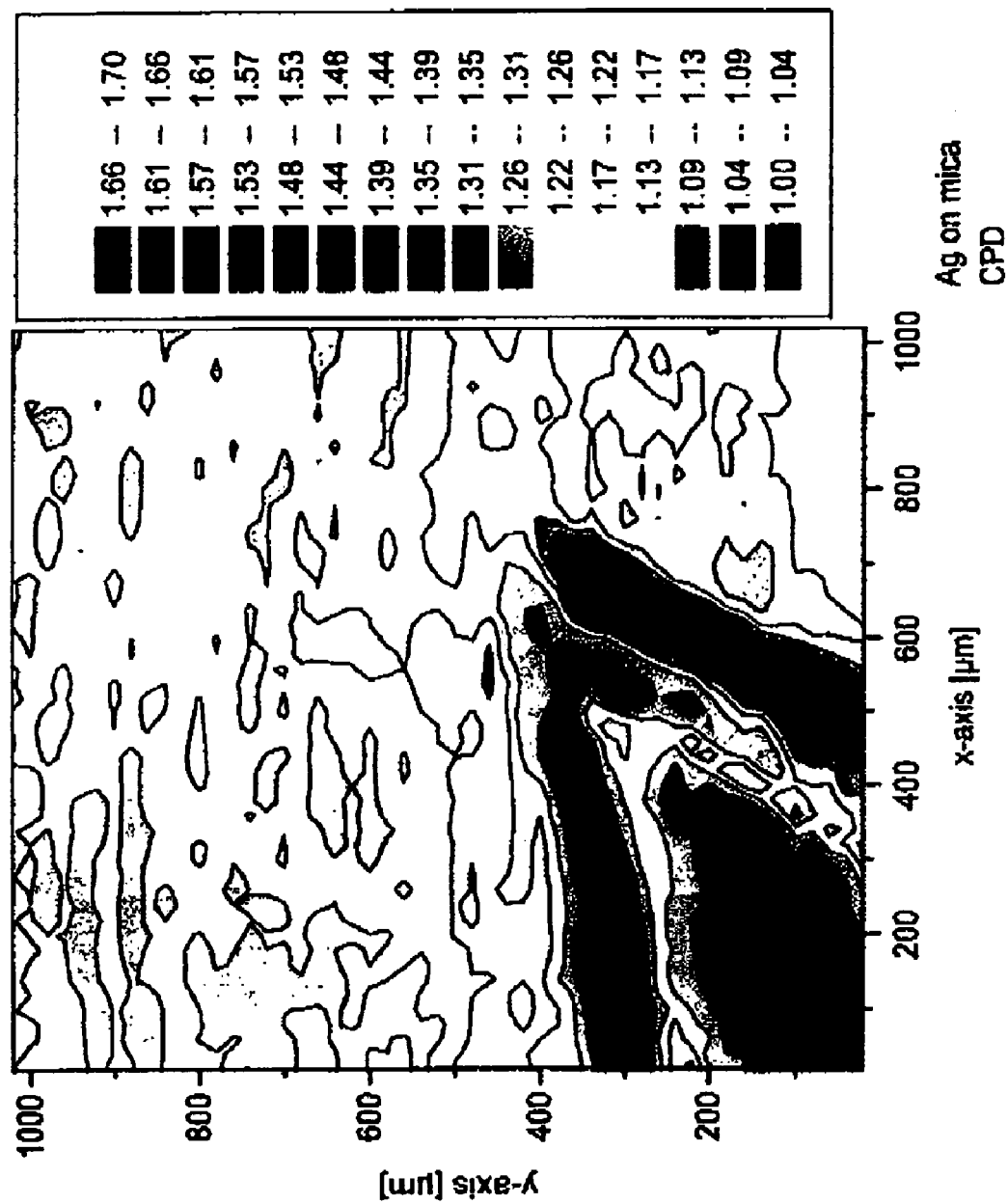
FIG. 6 is a CPD image of silver on a mica surface.
Figure 7:
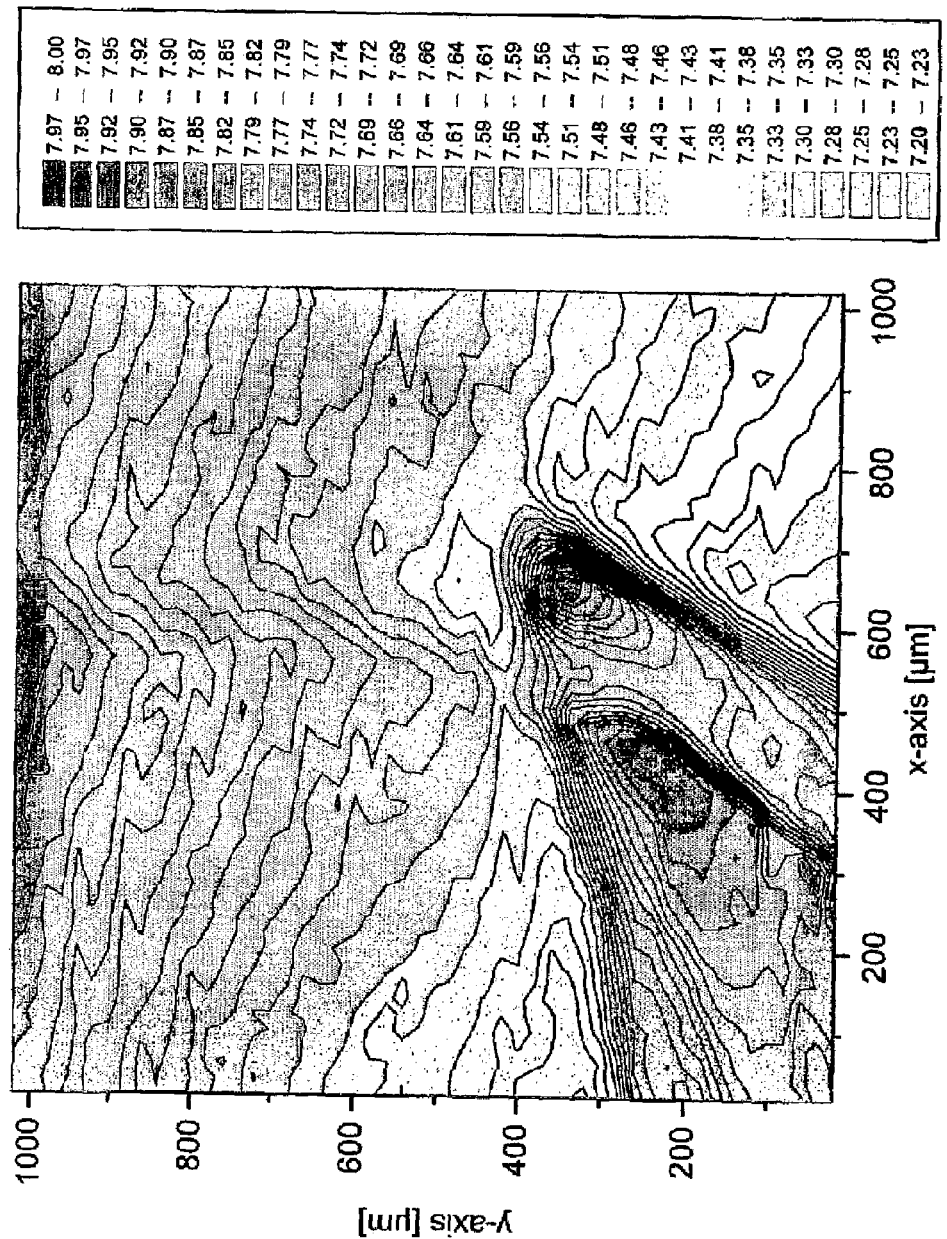
FIG. 7 illustrates the topography of silver on a mica surface.

FIG. 4 illustrates a CPD image obtained from a silver surface. FIG. 5 is a CPD image of a silver surface after surface treatment. FIG. 6 is a CPD image of silver on a mica surface. FIG. 7 illustrates the topography of silver on a mica surface.

Example 2

Characterizing Conductors

Figure 8:
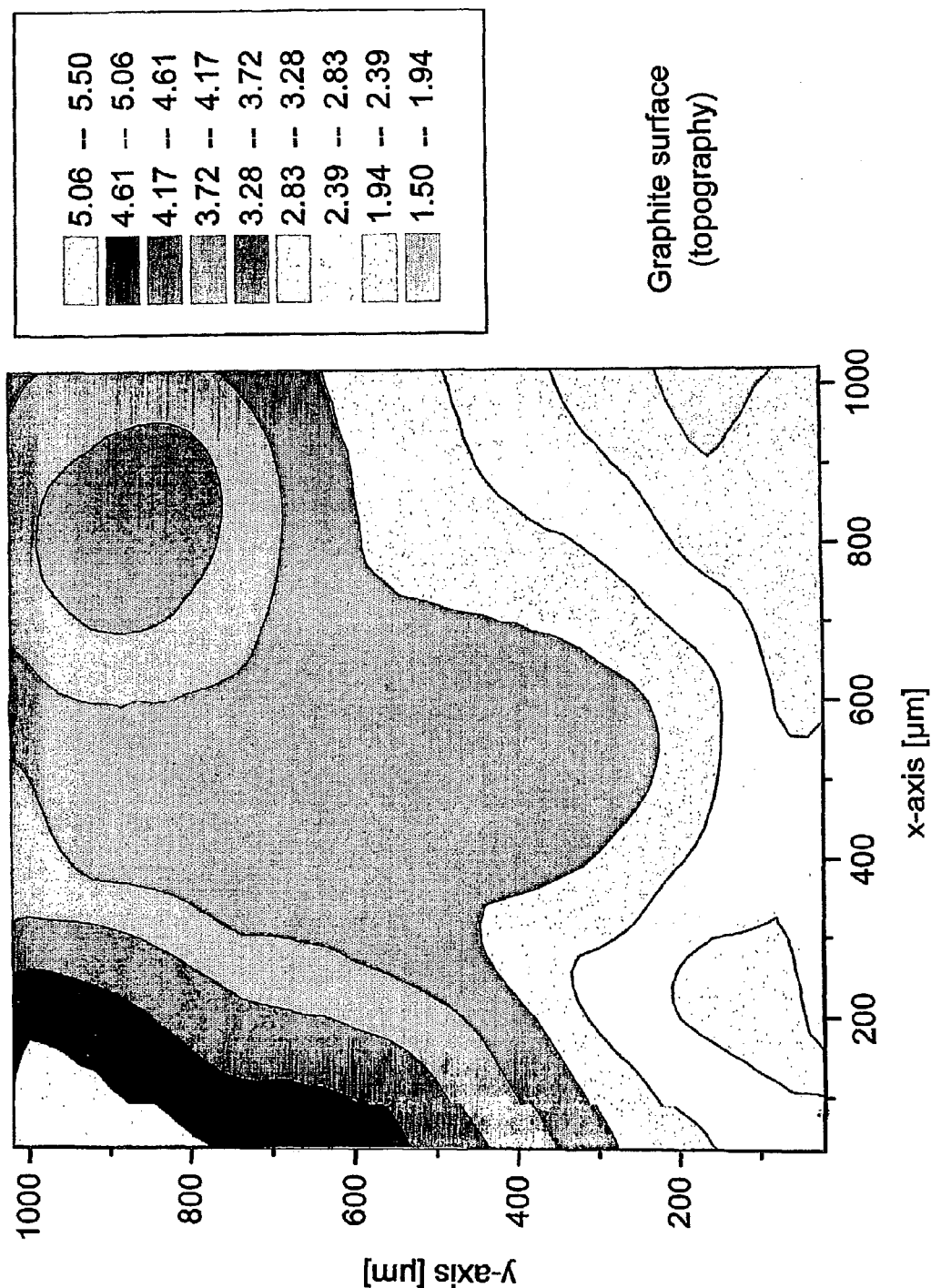
FIG. 8 illustrates the topography of a graphite surface.
Figure 9:
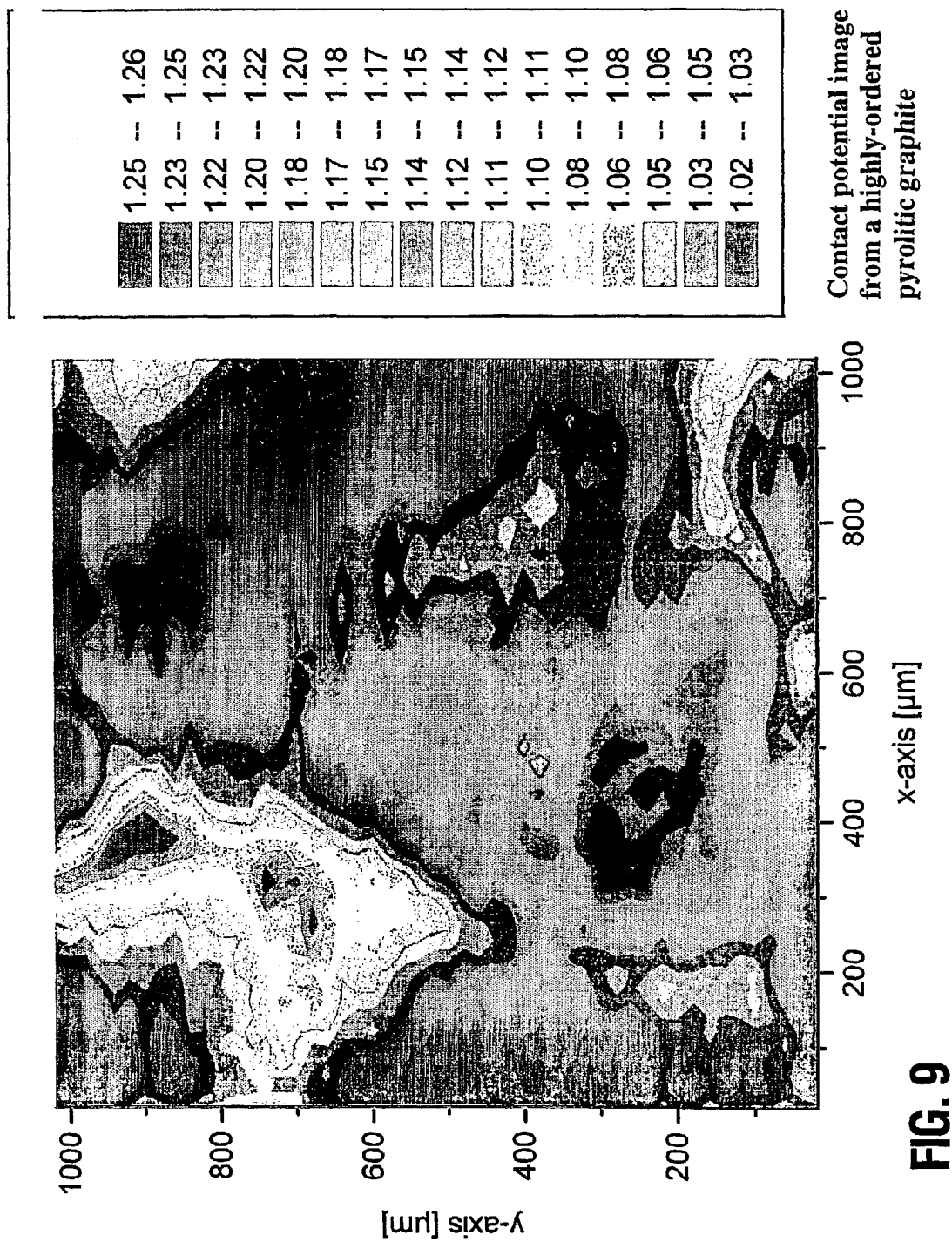
FIG. 9 is a CPD image of a highly-ordered pyrolitic graphite surface.

Highly ordered-pyrolitic graphite samples are analyzed. FIG. 8 illustrates the topography of a graphite surface. FIG. 9 is a CPD image of a highly-ordered pyrolitic graphite surface.

Example 3

Microelectronic Fabrication

Figure 10A:
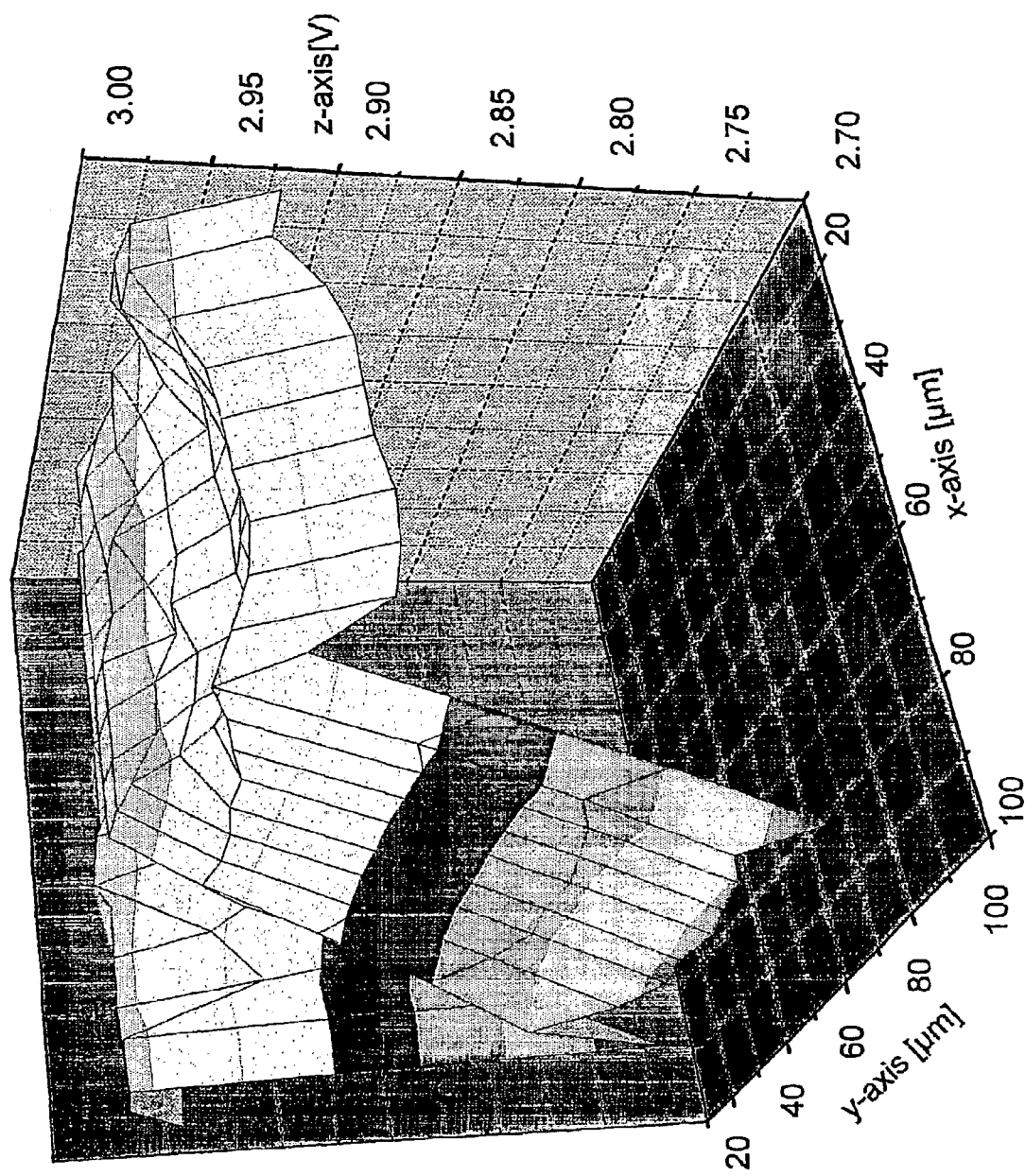
FIGS. 10A and 10B are depictions of tandem measurements of topography and CPD image, respectively, of patterned aluminum deposition on silicon wafer.
Figure 10B:
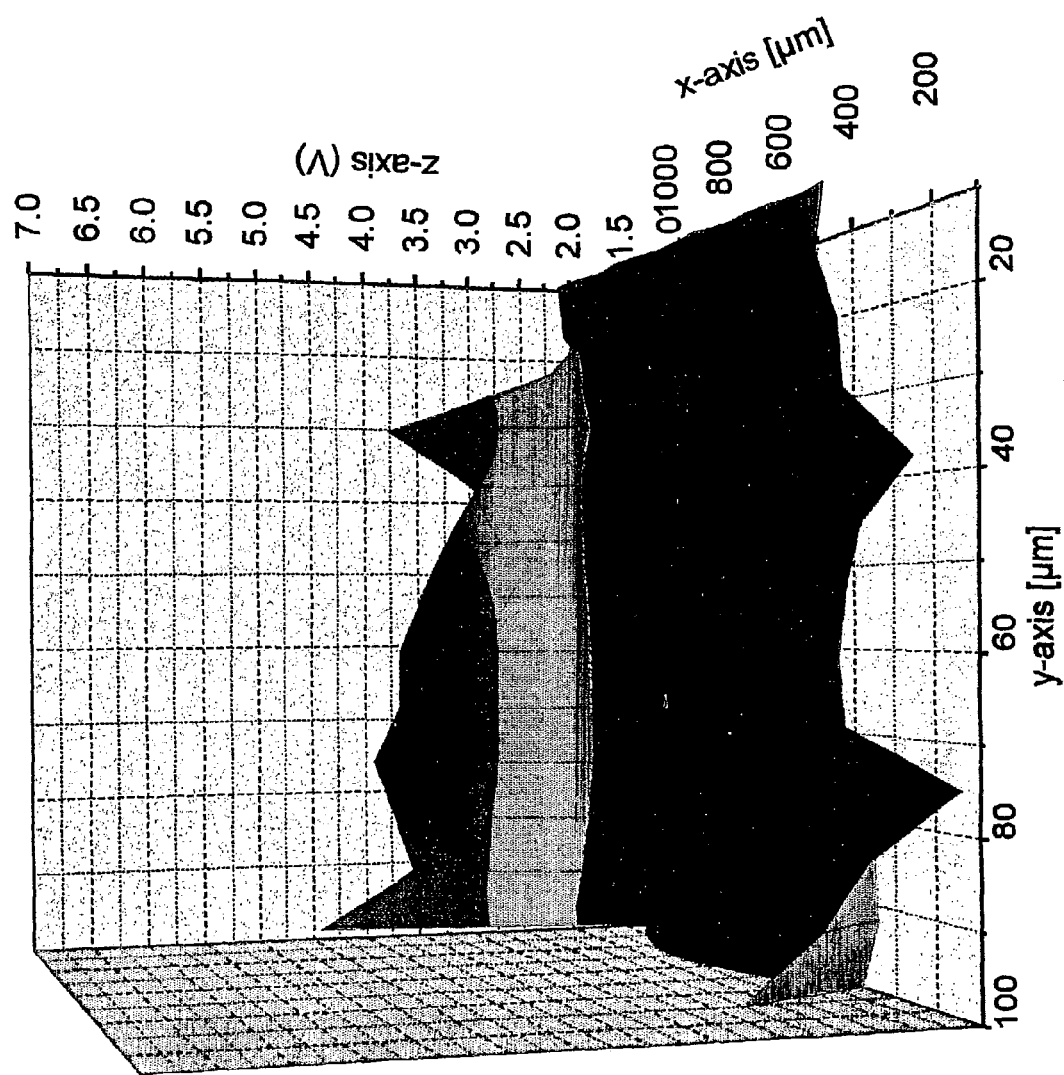

FIGS. 10A and 10B show a measure of the capabilities of the instrument by providing a tandem measurement of topography and CPD. FIG. 10A depicts a topographical image of the edge presented by a layer of aluminum deposited on a silicon wafer in a typical microelectronic fabrication process. The edge is supposed to be vertical with a steep height of about 1 µm. This particular topographical image was realised at a spatial resolution of 2 µm. Note that the second axis represents (in V) the displacement of the piezoelectric table and for 1V the piezoelectric material expands 20 µm. Accordingly, the aluminum layer appears to have a surface height variation of about 400 nm (0.02V). Secondly, it can be seen that the edge actually slopes over 20 µm (x-axis). FIG. 10B shows a tandem CPD image. Note that the image is both rotated at 90° and inverted in order to highlight the difference in contact potential between aluminum and silicon (the flat, bottom surface situated at 1.5V CPD is the aluminum surface). The technique as described herein does not generate absolute values of contact potential difference. Accordingly, the z-axis represents a relative scale of CPD values.

Example 4

Biosensor Technology

Reagents. The following chemicals were obtained from Aldrich and used as received: ω-Undecanoyl alcohol 98%, 6,6'-dithiodinicotinic acid, trifluoroacetic anhydride 99%, hydrogen hexachloroplatinate (IV) 99.99%, octadecyltrichlorosilane (OTS), trichlorosilane 99%, 3-mercaptopropyltrimethoxysilane (MPS), N-bromosuccinimide (NBS), 1,1'-azobis-(cyclohexanecarbonitrile)(ACN), and dimethylformamide-sulfurtrioxide complex. Various common solvents and chemicals were obtained from BDH and used without further treatment unless otherwise indicated as follows. Dichloromethane and acetonitrile, toluene and pyridine were distilled over $P_2O_5$, Na and KOH, respectively, and benzene and DMF were dried over molecular sieves before use.

Syntheses. 1-(thiotrifluoroacetato)-11-(trichlorosilyl)-undecane (TTU) was synthesized and characterized as described previously[16-19]. The sodium salt of 2.5-bis (bromomethyl) benzensulfonate (BMBS) was produced by bromomethylation of p-xylene followed by conversion to the sulfonate (sodium salt) with DMF-sulfurtrioxide reagent and NaOH.

Oligonucleotide syntheses of the following thiolated sequences 5'-HS-C6-TATAAAAAGAGAGAGATC-GAGTC-3' ($F_1$) and its single strand, un-thiolated complement ($F_2$), were performed using standard CE phosphoroamidite chemistry with conventional Applied Biosystems Inc. reagents. In order to produce the thiol-group containing oligonucleotide, an iodine solution was employed in conjunction with 3'-thiol modification cartridges (Glen Research). The oligonucleotides were purified using standard procedures with Poly-Pak cartridges purchased from Glen Research. The final products were checked for purity by HPLC and stored in 20% acetonitrile, in polypropylene vials. Solutions of $F_1$ were treated with a ten-fold excess of BMBS at neutral pH in order to produce an oligonucleotide-linker complex.

Procedures. Silicon surfaces were silanized in a dry box for 2 hours with 2 ml of a $10^{-3}$ M solution in dry toluene of a mixture of 30% TTU/70% OTS. The TTU coated wafers were treated with hydroxylamine in water (pH 8.5) for 2 hours to effect deprotection of the thiol group. The $F_1$ oligonucleotide was attached to the surface via the linker BMBS as described elsewhere[19]. Hybridization of the surface-bound oligonucleotide with its complementary strand was effected in pH 7.5 buffer at room temperature.

Surface immobilization of 25-mer oligonucleotides. The design and fabrication of biosensors capable of the detection of interfacial nucleic acid hybridization and interaction with small molecules such as drugs, regulatory peptides is an important area of study. This research activity requires the attachment of single strands of oligonucleotides to the device surface. A protocol extensively for achieving this involves nucleic acid-surface binding though interaction of chemisorbed neutravidin with biotinylated oligonucleotide. This method produces a surface nucleic acid density of only, at best, 1 pmol $cm^{-2}$ (compared to the maximum possible, for single strands, of about 100 pmol $cm^{-2}$)[18]. However, the sensitivity of device response can be enhanced by increasing nucleic acid surface density through silanization technology (on sensor chromium electrodes). The silane employed in the present experiments, to increase nucleic acid surface density, TTU, attaches to hydroxylated substrates by a self-assembly process to produce a near monolayer-like array of thiol functionalities (following de-protection of the sulfur-containing moieties). Dilution with OTS serves to minimize thiol-group cross linking interactions, and the use of a linking agent that forms disulfide bonds such as BMBS was found to optimize surface density of 11-mer oligonucleotides at about 50 pmol $cm^{-2}$ on silicon wafers[19].

Figure 11A:
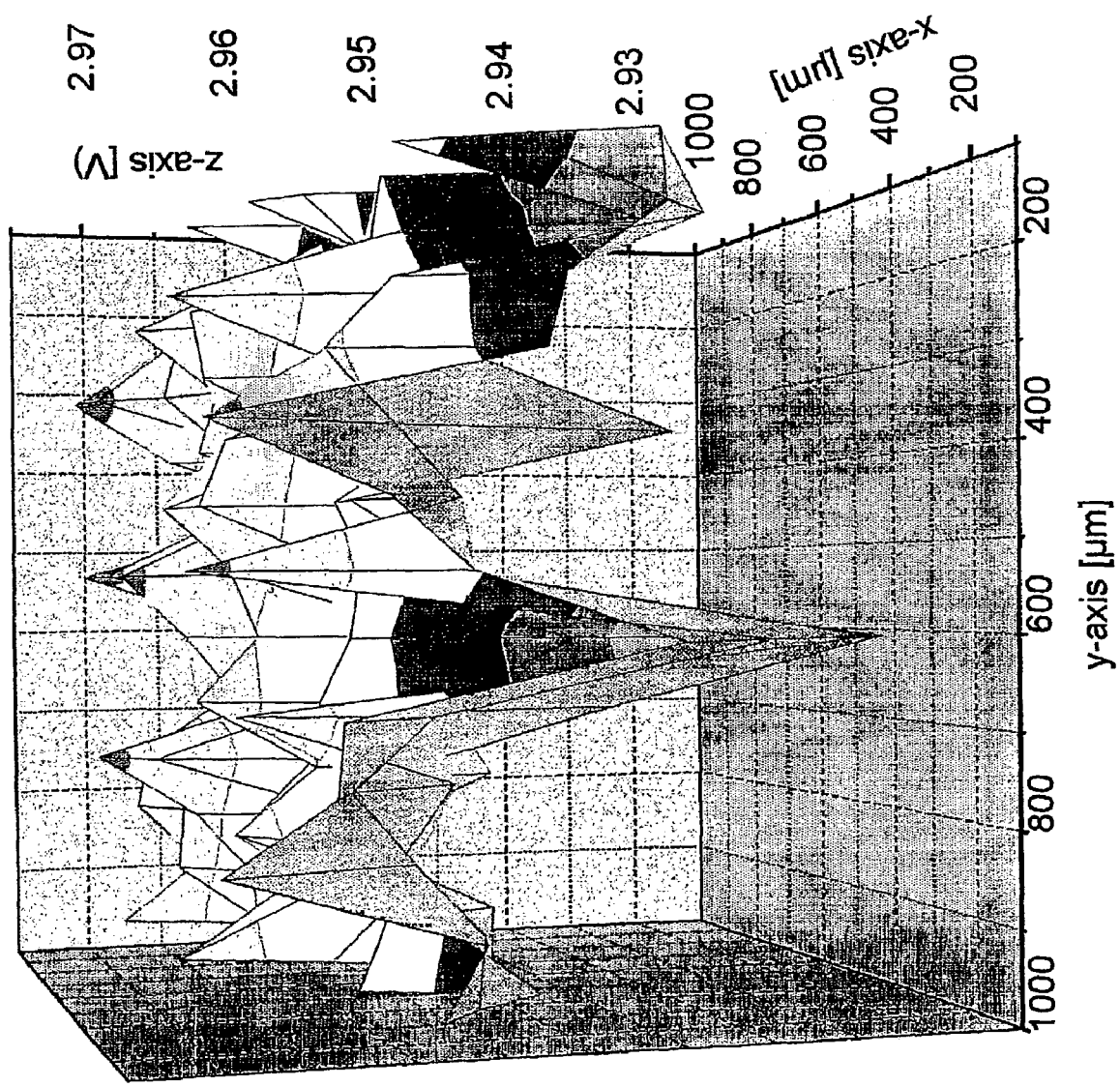
FIGS. 11A and 11B are depictions of tandem measurements of topography and CPD image, respectively, of a bare silicon wafer as an oligonucleotide substrate.
Figure 11B:
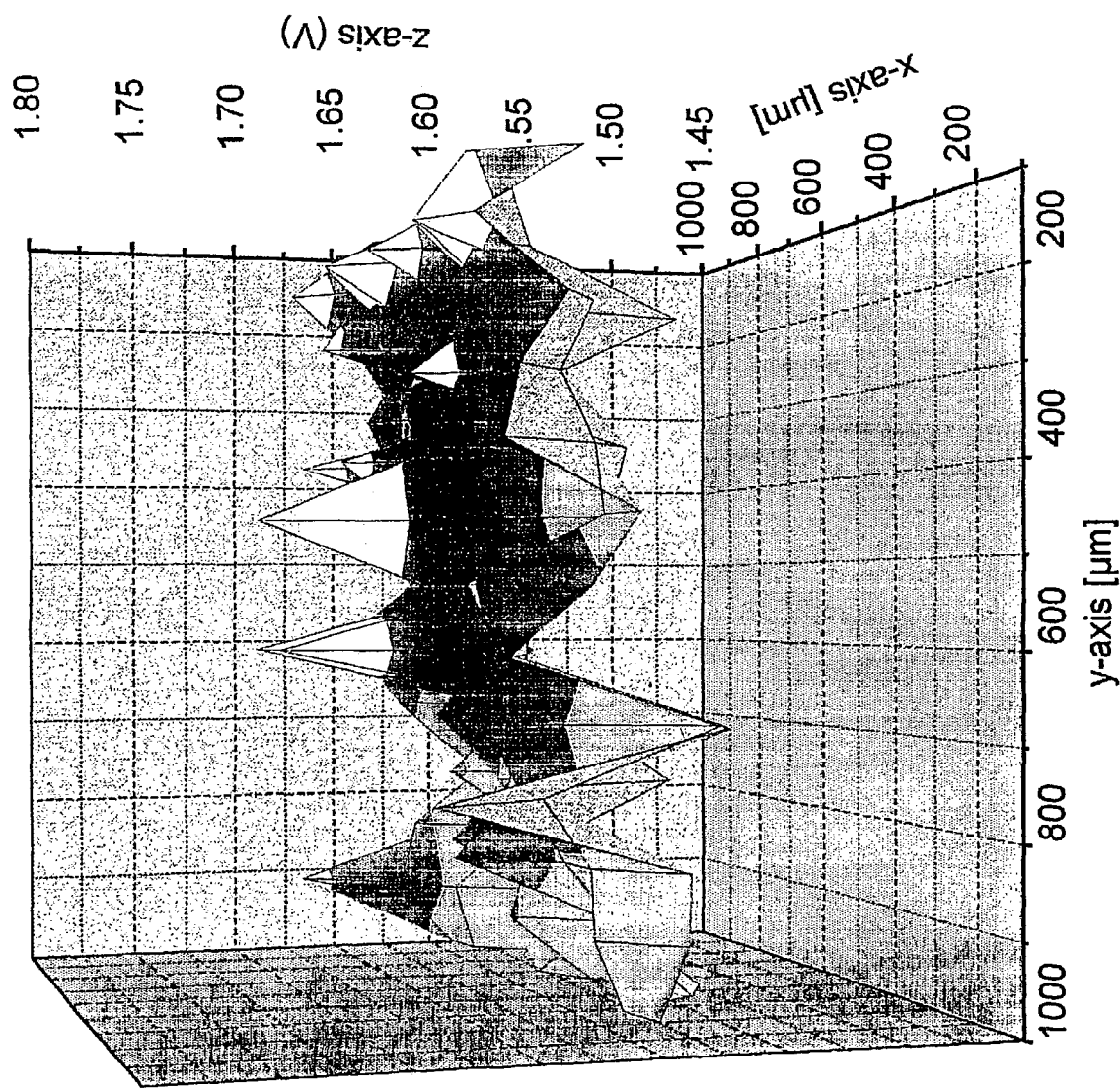

Silicon wafers obtained from International Wafer Service were supplied approximately 0.4 thick and were polished on one side to a mirror finish. They were cut to a size of about 1×1 cm using a diamond-tipped pencil. This experiment was conducted to obtain images that can serve as a control for any changes produced by subsequent surface chemical treatments. FIGS. 11A and 11B show the tandem topographical and CPD images obtained at 20 μm spatial resolution for the bare silicon wafer, respectively. The silicon wafer was later used for immobilizing nucleic acids. With respect to the topographical image, the picture was recorded viewing from the y-axis in order to isolate an obvious fissure of depth about 800 nm (width at half-depth is 100 μm). Aside from this structure, which is likely related to scratching connected to a polishing protocol, the surface height variability is of the order of 300 nm (0.15 V). The image also exhibits fairly uniform "peaks" with a half height dimension of about 100 nm. These characteristics are expected from a substrate surface that is considered to be optically flat. The CPD image shows a quite narrow range of surface variability of approximately of 75 mV, which is likely connected to differences in the level of oxidation and/or contamination from adventitious carbon. Note that the features on terms of spatial characteristics reflect the same overall picture as shown for the topographical image.

The immobilization of nucleic acids on biosensors and gene chips using TTU represents a new research area. The attachment of oligonucleotides to a silicon substrate was tested by employing the capabilities of the new SKM instrument.

Figure 12:
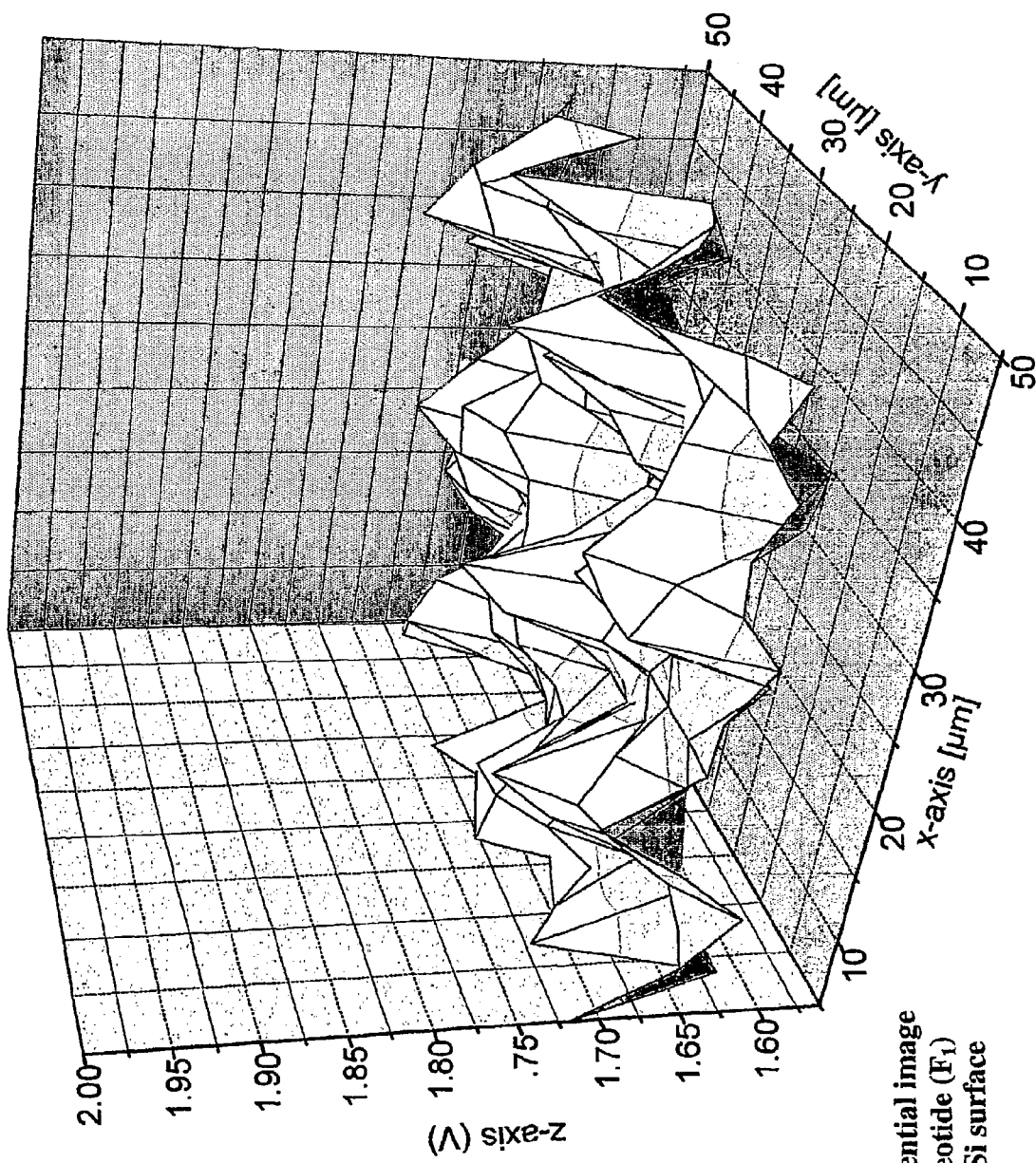
FIG. 12 is a CPD image of an oligonucleotide ($F_1$) attached to an Si surface according to an embodiment of the invention.

With respect to the use of Kelvin probe measurements to distinguish oligonucleotide and DNA duplex formation, the 25-mer probe, $F_1$, with BMBS linker in place, attaches to the de-protected TTU monolayer on the Si wafer through formation of a disulfide bond. Using this approach, the probe is disposed closer to the substrate surface at the 5'-end, whereas the 3'-terminus faces away from the interface. Experience has shown that the surface packing density attainable by this attachment protocol is of the order of 20 pmol $cm^{-2}$. This value implies that the surface density of attached nucleic acid is in the region of 1 molecule per 10 square nanometers. The precise orientation of the probe is unknown in terms of the air-to-solid interface. FIG. 12 shows the CPD image of Si surface-attached $F_1$ (1 μm resolution). The surface variability is in the range of about 100 mV with the mean value being 1.70 V. This represents a shift of approx. 80 mV per the average CPD value for the bare Si surface. There are "peaks" depicted in the image with widths at half-height of about 7 μm (spaced by 10 μM).

Figure 13:
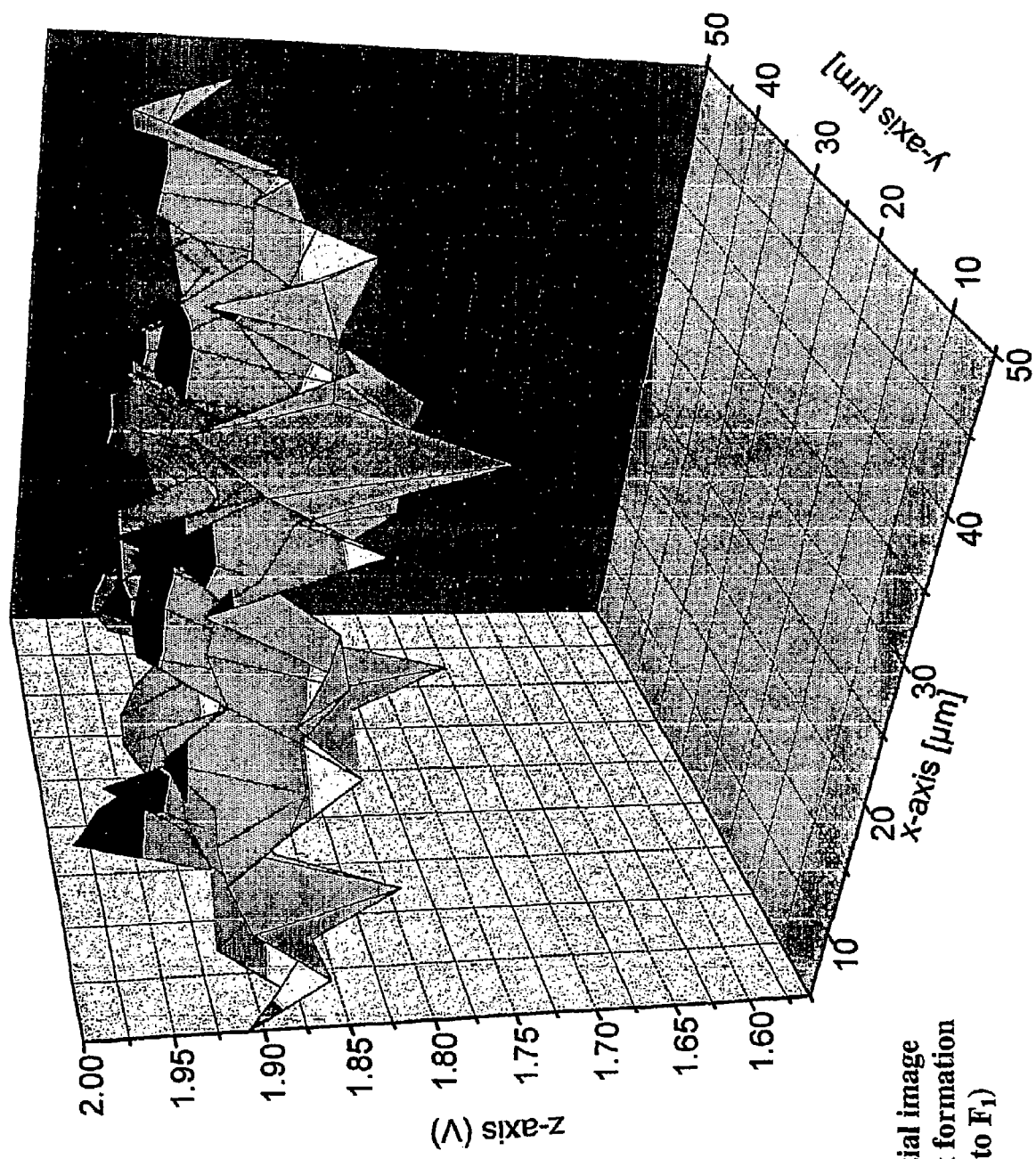
FIG. 13 is a CPD image of an $F_1$:$F_2$ duplex attached to an Si surface according to an embodiment of the invention.

FIG. 13 shows the CPD image of the same surface for $F_2$ hybridized to $F_1$. The overall surface variability and features are much the same as for the single strand 25-mer attached to the substrate, but the CPD value has shifted upward by over 200 mV. This result clearly indicates that detection of duplex formation by the SKM is feasible. Since the attainable resolution in relative CPD value is 1 mV, this result implies that high discrimination of the level of duplex formation connected to mismatches is feasible.

Example 5

Micromachined Devices, Thin-Films, and Self-Assembled Monolayers

This example is illustrative of the application of SKM according to the invention in characterization of micromachined devices, thin-films, and self-assembled monolayers. The properties of materials that form thin-films, self-assembled monolayers and microscopical structures appear to be different from those of a bulk material. Not only is scaling important in determining material and device properties in the micro-world, but also important are the relations between electrical and structural properties of the surface. Moreover, microminiaturization blurs the distinction between physical and chemical properties. Thus, the availability of new methods and advanced techniques for material characterization and device performance in the micro- and nano-worlds becomes imperative. SKM provides such a new technique, by offering a tandem electrical (through CPD measurements) and structural (topology) characterization.

Figure 14:
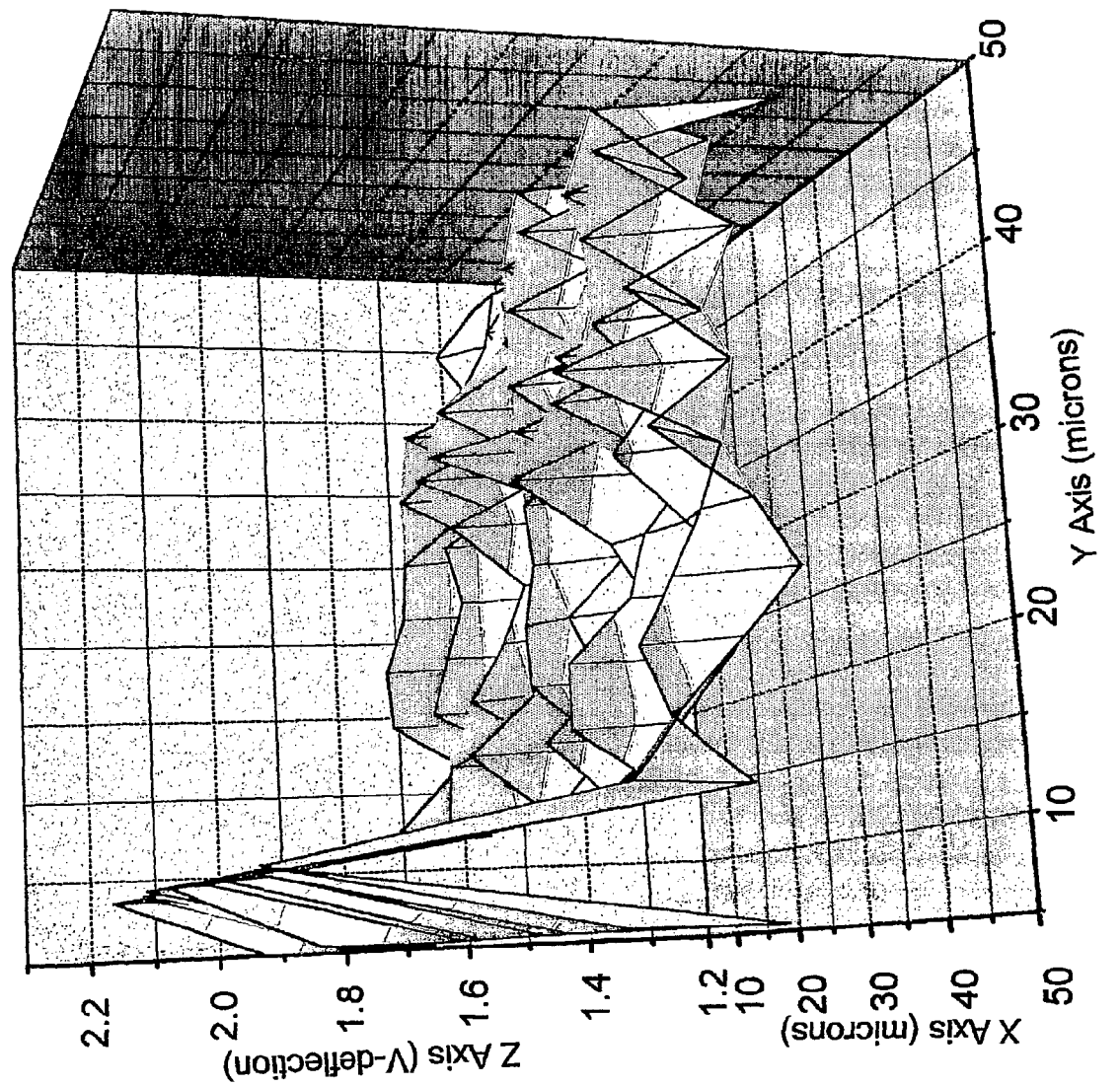
FIG. 14 depicts a topographical image of a micromachined structure patterned by laser micromachine technology on a TSM (Thickness-Shear Mode) sensor with one channel of 5 µm width.
Figure 15:
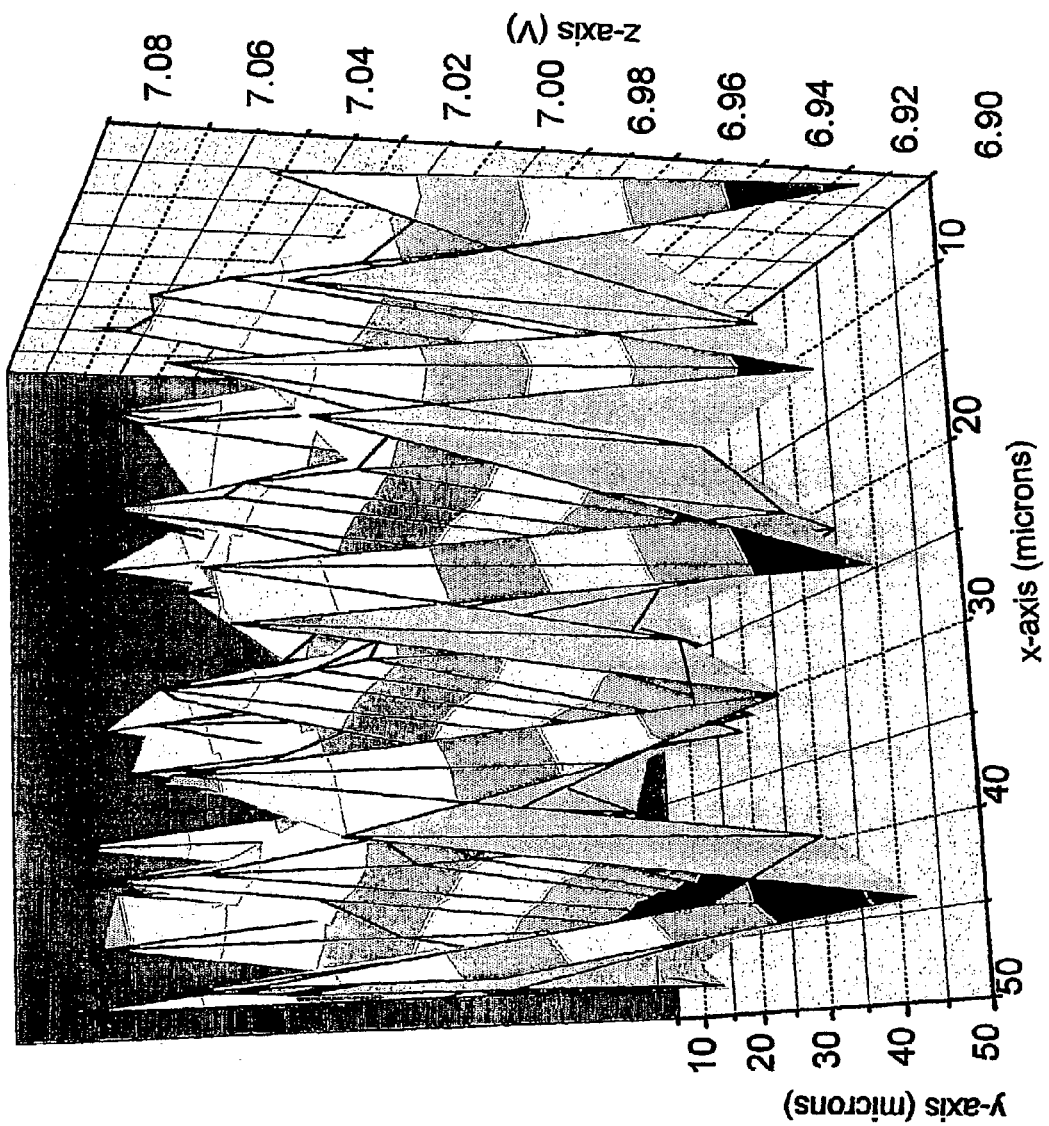
FIG. 15 depicts a topographical image of micromachined structure patterned by laser micromachine technology on a TSM (Thickness-Shear Mode) sensor with five channels of 5 µm width.

FIGS. 14 and 15 illustrate the application of SKM in micromachining. FIG. 14 represents a topographical image of micromachined structures patterned by laser micromachined technology on a TSM (Thickness-Shear Mode) sensor which were detected by the SKM technology disclosed here. FIG. 14 shows the image of a one channel of 5 μm width in the silicon surface Laser micromachining was used with a 5 micron line, a 40 micron space, and with a 1 micron lateral step. FIG. 15 shows the image of five channels of 5 μm width in the silicon surface. The 5 μm channels were formed in the silicon surface to change the electric field density, hence enhancing the signal and improving the functioning of the TSM. Lines of 5 micron were laser micromachined with a 1 micron lateral step. The SKM technology is facilitating the synergy provided by silicon fabrication techniques and biomolecule deposition to medical sensor devices in developing new applications and products of commercial interest.

Example 6

Characterizing Corroded Substrates

SKM can be employed in characterizing corroded substrates, with no special requirements being necessary. The measurement principle is based on the relationship between the surface potential and the corrosion potential, through the charge and dipole distribution at the interfaces. The SKM instrument can be used to obtain high lateral resolution that is needed to understand corrosion phenomena at micro- and nano-metric levels. Usual surface-analytical techniques can be used concomitantly.

In order to examine the potential of SKM in detecting corrosion, a piece of metal from Coca-Cola pop-can was investigated to assess the integrity of the paint layer that isolates the Al wall from the liquid, thus preventing the leaching of aluminum oxides (known as liver poisons) into the liquid. Images generated by SKM technology showed large islands of removed paint corroded by the liquid.

Example 7

Application in Determining Biocompatibility of Materials

Figure 16A:
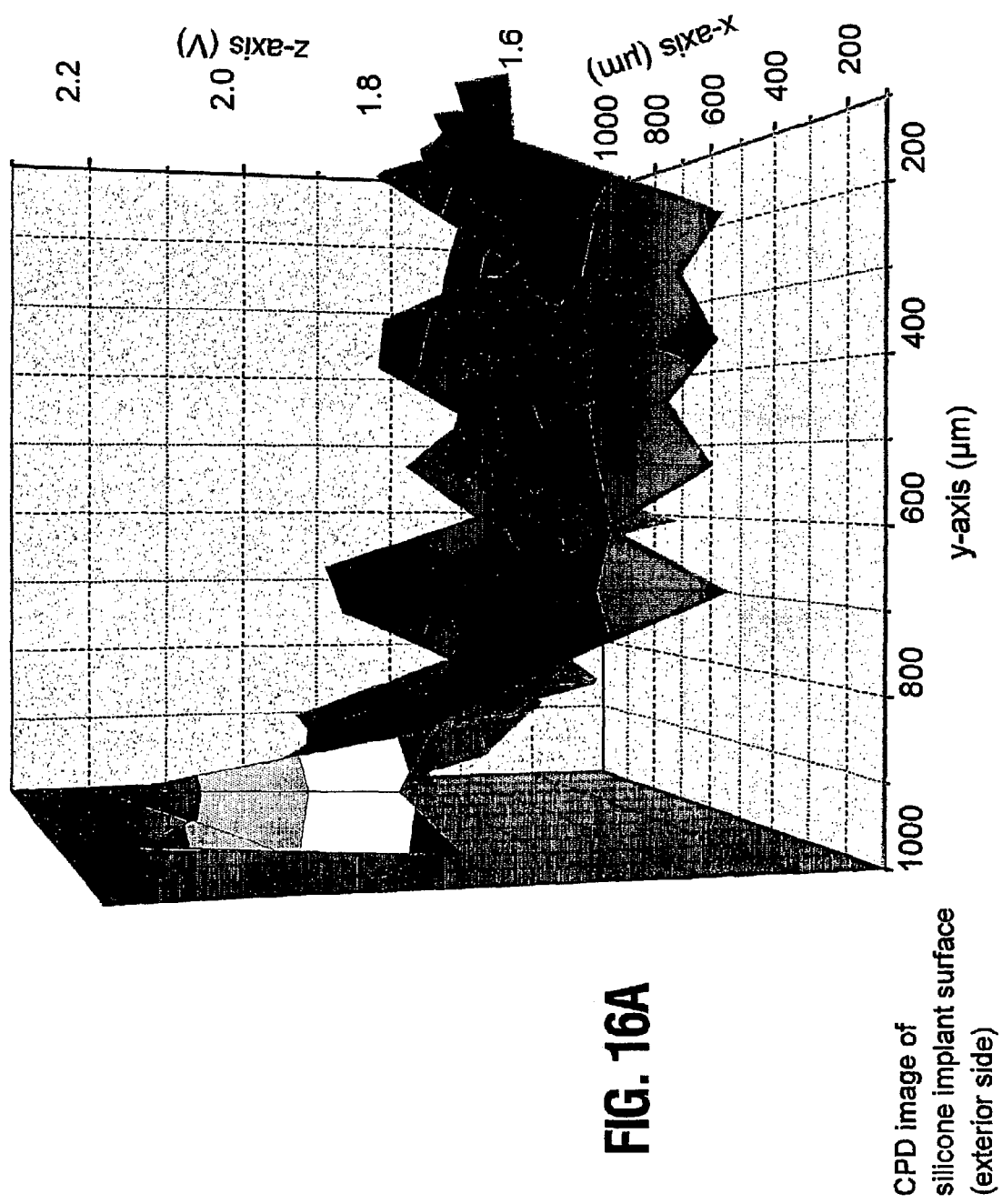
FIGS. 16A and 16B represent the CPD images of silicon-based polymer obtained from explanted breast implant that has been exposed to the inside surface, closest to the chest cavity (A), and to the biological tissue towards the outside (B).
Figure 16B:
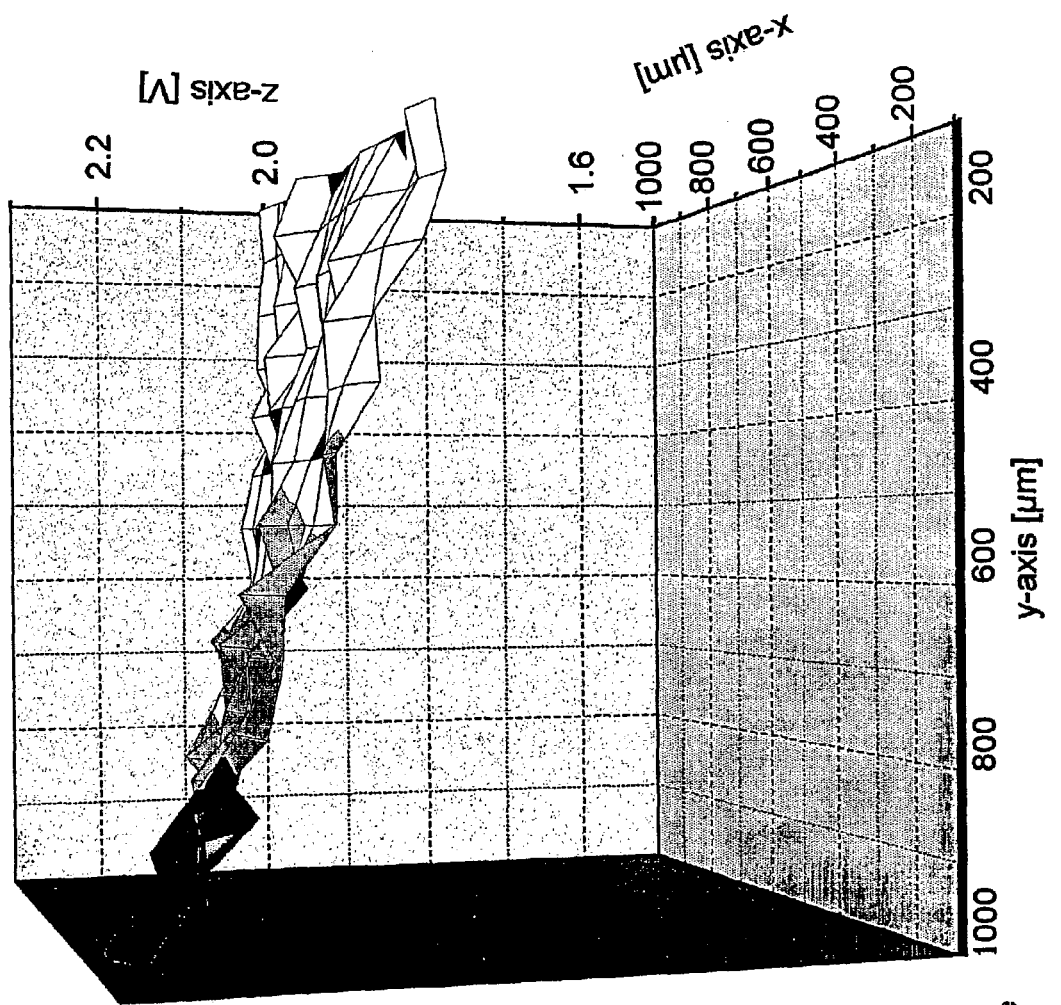

SKM was employed to determine biocompatibility of materials. FIGS. 16A and 16B show CPD images of samples of silicone polymer used in breast implants. The samples were from breast implants that were surgically removed from a patient who chose explantation due to controversy surrounding the medical consequences of silicon polymer-based-breast implants. Both the samples were obainted from the same implant. However, the one used for the image shown in FIG. 16A was isolated from the inside surface of the structure of the implant closest to the chest cavity, whereas the one used for the image shown in FIG. 16B was in contact with biological tissue towards the outside. The images demonstrate the power of the capability of SKM to represent CPD on a pseudo three-dimensional basis, that is, with spatial (xy plane) data plotted together with variation in actual CPD level (z plane). It is clear from the images that the surface exposed to different tissues possesses not only altered level of CPD, but also more variation than the other sample. Specifically, on average, the CPD values for the former surface are somewhat lower than the latter. In contrast, the topographical images of these samples exhibited identical smooth surfaces. The result demonstrates that the SKM can examine surface functional group chemistry, at the sub-micrometer level.

REFERENCES

1. L-E. Cheran, H-D. Liess, M. Thompson, *The Analyst*, 1999, 124, 961.
2. W. Nabhan, B. Eqer, A. Broniatowski and G. De Rosny, *Rev. Sci. Instrum.*, 1997, 68 (8), 3108.
3. M. Schmidt, M. Nohlen, G., Bermes, M. Bomer and K. Wandelt, *Rev. Sci. Instrum.*, 1997, 68, 10, 3866.
4. M. Bomisch, F. Burmeister, A. Rettenberg, J. Zimmermann, J. Boneberg and P. Leiderer, *J. Phys. Chem. B*, 1997, 101, 10162.
5. W. A. Zissman, *Rev. Sci. Instrum.*, 1932, 3, 367.
6. P. Craig and V. Radeka, *Rev. Sci. Instrum.*, 1970, 41, 2, 258.
7. N. A. Surplice and R. J. D'Arcy, *J. Phys. E: Sci. Instrum.*, 3,(1970), 477.
8. B. Ritty, F. Watchel, R. Manquenouille, F. Ott, J. Bonnet, *J. Phys. E: Sci. Instrum.*, 15, 1982, 310.
9. I. D. Baikie, E. Venderbosch, *Rev. Sci. Instrum.* 62 (3), 1991, 725.
10. O. A. Semenikhin, L. Jiang, T. Iyoda, K. Hashimoto, A. Fujishima, *J. Phys. Chem.* 100, 48, 1996, 18603.
11. I. Samec, W. Johnson, M. Cappadonia, M. Jauch, K. Doblhofer, *Sensors and Actuators, B*, 13–14 (1993) 741.
12. S. Lundgren, B. Kasemo, *Rev. Sci. Instrum.* 66, 7,(1995) 3976.
13. C. S. Kumar, A. Subrahmanyam, J. Majhi, Rev. Sci. Instrum. 67 (3) (1996), 805.
14. H. A. Engelhardt, P. Feulner, H. Pfnür, D. Menzel, *J. Phys E: Sci. Instr.* 19,(1977), 1133.
15. I. D. Baikie, G. H. Bruggink, *Mat. Res. Soc. Symp. Proc.* 309,(1993), 35.
16. M. E. McGovern, M. Thompson, *Can. J. Chem.* 77 (1999), 1678.
17. L. M. Furtado, H. Su, M. Thompson, D. P. Mack, G. L. Hayword, *Anal. Chem.* 7,(1999), 1167.
18. M. E. McGovern, M. Thompson, *Anal. Chem.*Submitted.
19. 20. M. Nonnenmacher, M. P. O'Boyle and H. K. Wickramasinghe, i Appl. Phys, Lett., 1991, 58, 25, 2921.
20. M. Nonnenmacher, M. P. O'Boyle and H. K. Wickramasinghe, *Ultramicroscopy*, 1992, 42–44, 268.
21. M. Yasutake, *J. Appl. Phys.*, 1995, 34, 3403.
22. M. Yasutake, A. Daisuke and M. Fujihira, *Thin Solid Films*, 1996, 723, 279.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A scanning Kelvin microprobe system for analyzing a surface of a sample, the system comprising:
   a tip with a predetermined work function for exploring a surface of the sample, and for extracting Kelvin current from a local capacitor toned between the tip and the sample, wherein the tip is a microelectrode having the apex radius of curvature less than about 100 nm;
   a piezoelectric element for vibrating the tip at a first frequency from about 1 to about 20 kHz;
   a scan table for placing the sample thereon;

a micropositioner for moving the scan table in x and y directions;

a piezoelectric translation stage attached to the scan table for moving the sample in the z direction for maintaining a constant sample-tip distance, a signal generator for directing vibration at a second frequency from about 100 to about 500 kHz, to control sample-tip distance for sample-tip capacitance detection;

an ultra low noise charge amplifier for converting the Kelvin current extracted by the tip into a voltage;

a first lock-in amplifier tuned at the a first frequency, for measuring the voltage and generating contact potential difference image signal;

a second lock-in amplifier tuned at the second frequency, for monitoring sample-tip distance and for generating a topographic image signal, the second frequency being above the first frequency, said first frequency and said second frequency being independently selected and non-interfering; and a controller comprising software for opening a file, initializing a card and a motor, starting the first and the second lock-in amplifiers, bringing the sample up, scanning the sample, bringing the sample down, writing data in a file, and closing the file; and a data acquisition system for acquiring said contact potential difference image signal and said topographical image signal.

2. The scanning Kelvin microprobe system according to claim 1, for analysis of a sample selected from the group consisting of conductors, semiconductors, insulators chemicals, biochemicals, photochemicals, chemical sensors, biosensors, biochemical microarrays, microelectronic devices, electronic image devices, micromachined devices, nanodevices, corroded materials, stressed materials, coatings, adsorbed materials, contaminated materials, oxides, thin films, and self assembling monolayers.

3. The scanning Kelvin microprobe system according to claim 1, wherein said radius of curvature is about 50 nm.

4. The scanning Kelvin microprobe system according to claim 1, wherein the first frequency is less than about 2 kHz and the second frequency is about 100 kHz.

* * * * *